United States Patent

Hiratsuka et al.

[11] Patent Number: 5,125,957
[45] Date of Patent: Jun. 30, 1992

[54] PYRIMIDINE DERIVATIVES

[75] Inventors: Mitsunori Hiratsuka, Takarazuka; Naonori Hirata, Sanda; Kazuo Saito; Hideyuki Shibata, both of Toyonaka, all of Japan

[73] Assignee: Sumitomo Chemical Company, Limited, Osaka, Japan

[21] Appl. No.: 602,689

[22] Filed: Oct. 24, 1990

[30] Foreign Application Priority Data

Nov. 1, 1989 [JP] Japan .................. 1-287133
May 30, 1990 [JP] Japan .................. 2-142390
Aug. 10, 1990 [JP] Japan .................. 2-213934

[51] Int. Cl.$^5$ ............... A01N 43/54; C07D 239/34; C07D 239/52; C07D 401/12
[52] U.S. Cl. ........................ 71/92; 71/90; 544/301; 544/316; 544/312; 544/3; 544/54; 544/58.5; 544/63; 544/96; 544/123; 540/467; 540/470; 540/481; 540/544; 540/575; 540/553; 540/601
[58] Field of Search ............ 71/92, 90; 544/301, 544/3, 63; 540/467, 544, 601

[56] References Cited

U.S. PATENT DOCUMENTS 4,248,619 2/1981 Serban et al. ................. 71/92

FOREIGN PATENT DOCUMENTS

| A39549 | 3/1989 | Australia . |
| 0223406 | 5/1987 | European Pat. Off. . |
| 0249707 | 12/1987 | European Pat. Off. . |
| 0249708 | 12/1987 | European Pat. Off. . |
| 0287072 | 10/1988 | European Pat. Off. . |
| 0287079 | 10/1988 | European Pat. Off. . |
| 0314623 | 5/1989 | European Pat. Off. . |
| 0315889 | 5/1989 | European Pat. Off. . |
| 0321846 | 6/1989 | European Pat. Off. . |
| 0335409 | 10/1989 | European Pat. Off. . |
| 0336494 | 10/1989 | European Pat. Off. . |
| 0346789 | 12/1989 | European Pat. Off. . |
| 0360163 | 3/1990 | European Pat. Off. . |
| 0372329 | 6/1990 | European Pat. Off. . |
| 0374839 | 6/1990 | European Pat. Off. . |
| 54-117486 | 6/1979 | Japan . |
| 63-258462 | 10/1988 | Japan . |
| 63-258463 | 10/1988 | Japan . |
| 63-258467 | 10/1988 | Japan . |
| 1-290671 | 11/1989 | Japan . |
| 2-56469 | 2/1990 | Japan . |

Primary Examiner—John M. Ford
Attorney, Agent, or Firm—Stevens, Davis, Miller & Mosher

[57] ABSTRACT

A pyrimidine derivative represented by the formula

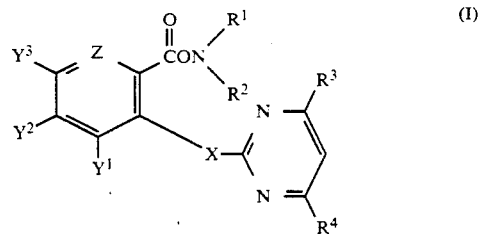

wherein the variables are defined below in the specification, and their production and herbicidal activities are described.

16 Claims, No Drawings

PYRIMIDINE DERIVATIVES

The present invention relates to a novel pyrimidine derivative, a method for producing the same, their use as herbicides and an intermediate of the same.

European Patent Application No. 0223 406Al, 0249 708Al, 0249 707Al, etc. disclose that pyrimidine derivatives can be used as an active ingredient for herbicides.

However, these compounds are not always said to be satisfactory because they are insufficient in herbicidal activity.

On the other hand, a large number of herbicides for crop lands or non-crop lands are now in use. However, there are many kinds of weed to be controlled and generation of the weeds extends over a long period of time, so that development of herbicides having a higher herbicidal effect and a broader herbicidal spectrum is being desired. Further, in recent years, no-till cultivation is carried out for the purposes of saving in labor, extension of cultivation period, prevention of soil running-off, etc. Because of this, it is being much desired to develop herbicides having both a high post-emergence herbicidal activity against weeds and a pre-emergence herbicidal activity excellent in residual effect, and besides having excellent selectivity of crops when crops are cultivated after application of herbicides.

In view of the situation like this, the present inventors have extensively studied, and as a result, have found that a pyrimidine derivative represented by the following formula (I) is a compound having excellent herbicidal activity, having few foregoing defects and some of them, having excellent selectivity between crops and weeds. That is the said pyrimidine derivative is a compound which can control weeds widely generated in crop lands or non-crop lands at low dosage rate, has a broad herbicidal spectrum and also can safely be used for no-till cultivation. The present invention is based on this finding.

The present invention provides a pyrimidine derivative represented by the formula (I) [hereinafter referred to as present compound(s)], a method for producing the same, their use as herbicides and an intermediate of the same:

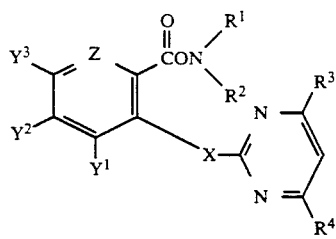

wherein each of $R^1$ and $R^2$, which may be the same or different, represents a hydrogen atom, a $C_1$-$C_6$ alkyl group, a $C_3$-$C_6$ alkenyl group, a $C_3$-$C_6$ alkynyl group, a halo $C_1$-$C_6$ alkyl group, a $C_1$-$C_6$ alkoxy $C_1$-$C_6$ alkyl group, a $C_3$-$C_6$ alkenyloxy $C_1$-$C_6$ alkyl group, a $C_3$-$C_6$ alkynyloxy $C_1$-$C_6$ alkyl group, a $C_1$-$C_6$ alkoxycarbonyl $C_1$-$C_6$ alkyl group, a $C_3$-$C_6$ alkenyloxycarbonyl $C_1$-$C_6$ alkyl group, a $C_3$-$C_6$ alkynyloxycarbonyl $C_1$-$C_6$ alkyl group, a cyano $C_1$-$C_6$ alkyl group, a group represented by the formula,

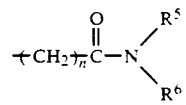

(in which each of $R^5$ and $R^6$, which may be the same or different, represents a hydrogen atom, a $C_1$-$C_6$ alkyl group, a $C_3$-$C_6$ alkenyl group or a $C_3$-$C_6$ alkynyl group, and n represents an integer of 1, 2, 3, or 4), a group represented by the formula,

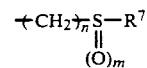

(in which n is as defined above, $R^7$ represents a $C_1$-$C_6$ alkyl group, a $C_3$-$C_6$ alkenyl group or a $C_3$-$C_6$ alkynyl group, and m represents an integer of 0, 1 or 2), a cyclo $C_3$-$C_8$ alkyl group, or an optionally substituted phenyl group, an optionally substituted benzyl group, or $R^1$ and $R^4$, bonded together at their ends, form an optionally substituted $C_4$-$C_7$ alkylene group or an optionally substituted $C_3$-$C_6$ alkylene group containing hetero atom; the hetero atom in $R^1$ and $R^2$ means a nitrogen atom, an oxygen atom or a sulfur atom; each of $R^3$ and $R^4$, which may be the same or different, represents a $C_1$-$C_6$ alkyl group, a $C_1$-$C_6$ alkoxy group, a halo $C_1$-$C_6$ alkoxy group or a halogen atom; X represents an oxygen atom or a sulfur atom; Z represents N or $CY^4$; each of $Y^1$, $Y^2$, $Y^3$, which may be the same or different, represents a hydrogen atom, a halogen atom, a $C_1$-$C_6$ alkyl group, or a $C_1$-$C_6$ alkoxy group; and $Y^4$ represents a hydrogen atom, a hydroxyl group, a mercapto group, a nitro group, a halogen atom, a $C_1$-$C_6$ alkyl group, a $C_2$-$C_6$ alkenyl group, a $C_2$-$C_6$ alkynyl group, a $C_1$-$C_6$ alkoxy group, a $C_3$-$C_6$ alkenyloxy group, a $C_3$-$C_6$ alkynyloxy group, a halo $C_1$-$C_6$ alkyl group, a halo $C_2$-$C_6$ alkenyl group, a halo $C_2$-$C_6$ alkynyl group, a halo $C_1$-$C_6$ alkoxy group, a halo $C_3$-$C_6$ alkenyloxy group, a halo $C_3$-$C_6$ alkynyloxy group, a $C_1$-$C_6$ alkoxy $C_1$-$C_6$ alkyl group, a $C_3$-$C_6$ alkenyloxy $C_1$-$C_6$ alkyl group, a $C_3$-$C_6$ alkynyloxy $C_1$-$C_6$ alkyl group, a cyano group, a formyl group, a carboxyl group, a $C_1$-$C_6$ alkoxycarbonyl group, a $C_3$-$C_6$ alkenyloxycarbonyl group, a $C_3$-$C_6$ alkynyloxycarbonyl group; an optionally substituted phenyl group, an optionally substituted phenoxy group, an optionally substituted phenylthio group, an optionally substituted benzyloxy group, an optionally substituted benzylthio group, a group represented by the formula,

(in which $R^5$ and $R^6$ are as defined above), a group represented by the formula,

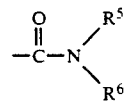

(in which $R^5$ and $R^6$ are as defined above),

(in which $R^7$ and m are as defined above), a group represented by the formula,

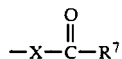

(in which $R^7$ and X are as defined above), or a group represented by the formula,

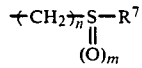

(in which $R^7$, m and n are as defined above), each optionally substituted group in the above being substituted with a $C_1$-$C_6$ alkyl group, a $C_1$-$C_6$ alkoxy group, a halo $C_1$-$C_6$ alkyl group, a $C_1$-$C_6$ alkoxycarbonyl group or a halogen atom. In the compound of the formula (I), the substituents $R^3$ and $R^4$, which may be the same or different, are preferably a $C_1$-$C_6$ alkoxy group, and more preferably, both of them are a methoxy group. X is preferably an oxygen atom. Z is preferably N or $CY^5$ [in which $Y^5$ represents a hydrogen atom, a halo $C_1$-$C_6$ alkyl group, or a halogen atom. More preferably Z is $CY^5$ and $Y^5$ is a halo $C_1$-$C_6$ alkyl group or a halogen atom, and more preferably $Y^5$ is a halogen atom. $Y^1$, $Y^2$ and $Y^3$ are preferably a hydrogen atom or a fluorine atom.

Specific examples of the pyrimidine derivative of the present invention include 4,6-dimethoxy-2-{2-(N,N-dimethylaminooxycarbonyl)-phenoxy}pyrimidine, 4,6-dimethoxy-2-{3-chloro-2-(N,N-dimethylaminooxycarbonyl)phenoxy}pyrimidine, 4,6-dimethoxy-2-{3-fluoro-2-(N,N-dimethylaminooxycarbonyl)phenoxy}pyrimidine, 3-(4,6-dimethoxypyrimidin-2-yl)oxy-2-(N,N-dimethylaminooxycarbonyl)pyridine, 4,6-dimethoxy-2-{3-trifluoromethyl-2-(N,N-dimethylaminooxycarbonyl)phenoxy}pyrimidine, 4,6-dimethoxy-2-{3-chloro-2-(1-piperidyloxycarbonyl)-phenoxy}pirimidine, 4,6-dimethoxy-2-{3-chloro-2-(N-tert-butylaminooxycarbonyl)phenoxy}pirimidine.

A method for producing the present compound is as follows.

The present compound (I) can be produced by reacting a phenol derivative represented by the formula (II),

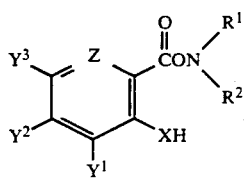

wherein $R^1$, $R^2$ X, $Y^1$, $Y^2$, $Y^3$ and Z are as defined above], with a pyrimidine derivative represented by the formula (III),

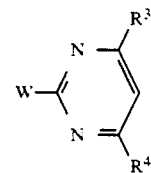

[wherein $R^3$ and $R^4$ are each as defined above and W represents a halogen atom or a group represented by the formula,

(in which $R^8$ represents a $C_1$-$C_6$ alkyl group or an benzyl group which being optionally substituted with $C_1$-$C_6$ alkyl group $C_1$-$C_6$ alkoxy group, a halogen atom or a nitro group, and m represents an integer of 0, 1 or 2).

This reaction is usually carried out with or without a solvent in the presence of a base. The reaction temperature ranges from room temperature to the boiling point of the solvent, and the reaction time ranges from 10 minutes to 24 hours. Referring to the amounts of the reagents used for this reaction, the amount of the pyrimidine derivative (III) is 1.0 to 1.5 equivalents based on 1 equivalent of the phenol derivative (II), and that of the base is 1.0 to 5.0 equivalents based on the same. The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), alcohols (e.g. methanol, ethanol, isopropanol, tert-butanol, octanol, cyclohexanol, methyl cellosolve, diethylene glycol, glycerin), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), liquid ammonia, water and mixtures thereof.

The base includes organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired present compound can be obtained.

The pyrimidine derivative represented by the formula (III) can be produced according to Japanese Patent Application Kokai No. 63-23870, J. Org. Chem., 26, 792 (1961), etc.

The present compound can also be produced by reacting [reaction (i)] a pyrimidine derivative represented by the formula (IV),

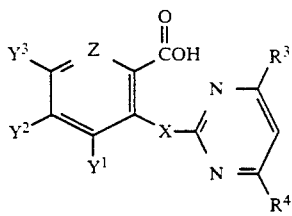

(IV)

wherein $R^3$, $R^4$, X, $Y^1$, $Y^2$, $Y^3$ and Z are as defined above], with an acid-halogenating agent or an active esterifying agent, and subsequently reacting [reaction (ii)] the resulting reaction product with a hydroxylamine derivative represented by the formula (V),

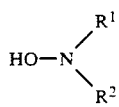

(V)

(wherein $R^1$ and $R^2$ are as defined above.)

In the above reaction (i), the acid-halogenating agent includes thionyl chloride, thionyl bromide, phosphorus trichloride, phosphorus tribromide, phosphorus pentachloride, phosphorus oxychloride, phosgene, oxalic acid dichloride, etc. The active esterifying agent includes N,N'-disubstituted carbodiimides such as N,N'-dicyclohexylcarbodiimide, N,N'-diisopropylcarbodiimide, 1-ethyl-3-(3-dimethylaminopropyl)carbodiimide hydrochloride, etc.; arylsulfonyl chlorides such as 2,4,6-trimethylbenzenesulfonyl chloride, 2,4,6-triisopropylbenzenesulfonyl chloride, etc.; N,N'-carbonyldiimidazole; diphenylphosphorylazide; N-ethoxycarbonyl-2-ethoxy-1,2-dihydroquinoline; N-ethyl-2'-hydroxybenzisoxazolium trifluoroborate; N-ethyl-5-phenylisoxazolium-3'-sulfonate; etc.

By this reaction, a pyrimidine derivative represented by the formula (VI),

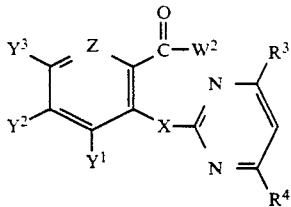

(VI)

wherein $R^3$, $R^4$, X, $Y^1$, $Y^2$, $Y^3$ and Z are as defined above, is produced in the reaction system.

In the above formula (VI), a substituent $W^2$ represents a halogen atom when the acid-halogenating agent was used; $W^2$ represents an N,N'-disubstituted-2-isoureide group when N,N'-disubstituted carbodiimide was used as the active esterifying agent; $W^2$ represents an arylsulfonyloxy group when arylsulfonyl chloride was used as said agent; $W^2$ represents an imidazolyl group when N,N'-carbonyldiimidazole was used as said agent; $W^2$ represents an azide group when diphenylphosphorylazide was used as said agent; $W^2$ represents an ethoxycarbonyloxy group when N-ethoxycarbonyl-2-ethoxy-1,2-dihydroquinoline was used as said agent; $W^2$ represents a 3-(N-ethylaminocarbonyl)-2-hydroxyphenoxy group when N-ethyl- 2'-hydroxybenzisox-azolium trifluoroborate was used as said agent; and $W^2$ represents a group

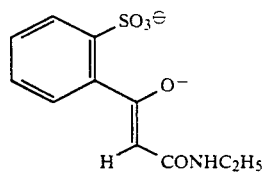

when N-ethyl-5-phenylisoxazolium-3'-sulfonate was used as said agent

In the reaction system, $W^2$ can also take a form of acid anhydride represented by the formula,

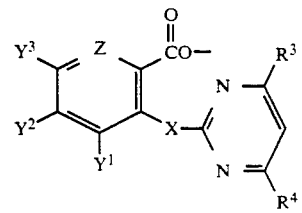

(wherein $R^3$, $R^4$, X, $Y^1$, $Y^2$, $Y^3$ and Z are as defined above.)

The amount of the foregoing acid-halogenating agent or active esterifying agent used is usually 1 to 10 equivalents based on 1 equivalent of the pyrimidine derivative represented by the formula (IV).

The amount of the hydroxylamine derivative of the formula (V) used is usually 1 to 5 equivalents based on 1 equivalent of the pyrimidine derivative represented by the formula (IV).

The reactions (i) and (ii) can also be carried out, if necessary, in the presence of a base. Such a base includes organic bases (e.g. 1-methylimidazole, 3-nitro-1H-1,2,4-triazole, 1H-tetrazole, 1H-1,2,4-triazole, imidazole, pyridine, triethylamine) and inorganic bases (e.g. potassium carbonate). The amount of the base used is 1 to 20 equivalents based on 1 equivalent of the pyrimidine derivative represented by the formula (IV).

The reactions (i) and (ii) are usually carried out in the presence of an inert solvent. Such a solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. N,N-dimethylformamide), sulfur compounds (e.g. dimethyl sulfoxide, sulfolane) and mixtures thereof.

Generally, the reaction temperature ranges from 0° C. to the boiling point of the solvent in any of the reactions (i) and (ii). The reaction time ranges from 1 to 24 hours for each reaction, and from about 1 to about 48 hours through the reactions (i) and (ii).

After completion of the reaction, the reaction solution is after-treated as usual. That is, water is added to the solution which is then extracted with an organic solvent and concentrated, and if necessary, the product obtained is subjected to the chromatography, distillation, recrystallization, etc. Thus, the desired present compound can be obtained.

The pyrimidine derivative represented by the formula (IV) can be produced according to Japanese Patent Application Kokai No. 62-174059, etc.

Table 1 illustrates examples of the compound (I) which can be produced by the above procedures.

TABLE 1

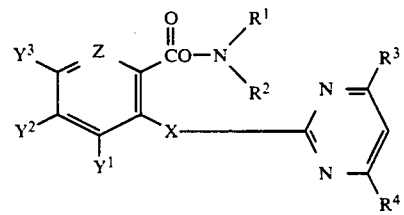

| $R^1$ | $R^2$ | $Y^1$ | $Y^2$ | $Y^3$ | Z | X | $R^3$ | $R^4$ |
|---|---|---|---|---|---|---|---|---|
| H | H | H | H | H | CH | O | $OCH_3$ | $OCH_3$ |
| H | H | H | H | H | N | O | $OCH_3$ | $OCH_3$ |
| H | H | H | H | H | CCl | O | $OCH_3$ | $OCH_3$ |
| H | H | H | H | H | CF | O | $OCH_3$ | $OCH_3$ |
| H | $CH_3$ | H | H | H | CH | O | $OCH_3$ | $OCH_3$ |
| H | $CH_3$ | H | H | H | N | O | $OCH_3$ | $OCH_3$ |
| H | $CH_3$ | H | H | H | CCl | O | $OCH_3$ | $OCH_3$ |
| H | $CH_3$ | H | H | H | CF | O | $OCH_3$ | $OCH_3$ |
| $CH_3$ | $CH_3$ | H | H | H | CH | O | $OCH_3$ | $OCH_3$ |
| $CH_3$ | $CH_3$ | H | H | H | CH | S | $OCH_3$ | $OCH_3$ |
| $CH_3$ | $CH_3$ | H | H | H | CH | O | Cl | $OCH_3$ |
| $CH_3$ | $CH_3$ | H | H | H | CH | O | $CH_3$ | $CH_3$ |
| $CH_3$ | $CH_3$ | $CH_3$ | H | H | CH | O | $OCH_3$ | $OCH_3$ |
| $CH_3$ | $CH_3$ | H | $CH_3$ | H | CH | O | $OCH_3$ | $OCH_3$ |
| $CH_3$ | $CH_3$ | H | H | $CH_3$ | CH | O | $OCH_3$ | $OCH_3$ |
| $CH_3$ | $CH_3$ | H | H | H | $CCH_3$ | O | $OCH_3$ | $OCH_3$ |
| $CH_3$ | $CH_3$ | H | H | H | $CC_2H_5$ | O | $OCH_3$ | $OCH_3$ |
| $CH_3$ | $CH_3$ | $OCH_3$ | H | H | CH | O | $OCH_3$ | $OCH_3$ |
| $CH_3$ | $CH_3$ | H | $OCH_3$ | H | CH | O | $OCH_3$ | $OCH_3$ |
| $CH_3$ | $CH_3$ | H | H | $OCH_3$ | CH | O | $OCH_3$ | $OCH_3$ |
| $CH_3$ | $CH_3$ | H | H | H | $COCH_3$ | O | $OCH_3$ | $OCH_3$ |
| $CH_3$ | $CH_3$ | F | H | H | CH | O | $OCH_3$ | $OCH_3$ |
| $CH_3$ | $CH_3$ | H | F | H | CH | O | $OCH_3$ | $OCH_3$ |
| $CH_3$ | $CH_3$ | H | H | F | CH | O | $OCH_3$ | $OCH_3$ |
| $CH_3$ | $CH_3$ | H | H | H | CF | O | $OCH_3$ | $OCH_3$ |
| $CH_3$ | $CH_3$ | H | H | H | CF | O | $OCH_3$ | Cl |
| $CH_3$ | $CH_3$ | H | H | F | CF | O | $OCH_3$ | $OCH_3$ |
| $CH_3$ | $CH_3$ | F | H | H | CF | O | $OCH_3$ | $OCH_3$ |
| $CH_3$ | $CH_3$ | F | H | F | CF | O | $OCH_3$ | $OCH_3$ |
| $CH_3$ | $CH_3$ | Cl | H | H | CH | O | $OCH_3$ | $OCH_3$ |
| $CH_3$ | $CH_3$ | H | Cl | H | CH | O | $OCH_3$ | $OCH_3$ |
| $CH_3$ | $CH_3$ | H | H | Cl | CH | O | $OCH_3$ | $OCH_3$ |
| $CH_3$ | $CH_3$ | H | H | H | CCl | O | $OCH_3$ | $OCH_3$ |
| $CH_3$ | $CH_3$ | H | H | F | CCl | O | $OCH_3$ | $OCH_3$ |
| $CH_3$ | $CH_3$ | H | H | H | CBr | O | $OCH_3$ | $OCH_3$ |
| $CH_3$ | $CH_3$ | H | H | H | CI | O | $OCH_3$ | $OCH_3$ |
| $CH_3$ | $CH_3$ | H | H | H | COH | O | $OCH_3$ | $OCH_3$ |
| $CH_3$ | $CH_3$ | H | H | H | CSH | O | $OCH_3$ | $OCH_3$ |
| $CH_3$ | $CH_3$ | H | H | H | $CNO_2$ | O | $OCH_3$ | $OCH_3$ |
| $CH_3$ | $CH_3$ | H | H | H | $CCH=CH_2$ | O | $OCH_3$ | $OCH_3$ |
| $CH_3$ | $CH_3$ | H | H | H | $CC\equiv CH$ | O | $OCH_3$ | $OCH_3$ |
| $CH_3$ | $CH_3$ | H | H | H | $COC_2H_5$ | O | $OCH_3$ | $OCH_3$ |
| $CH_3$ | $CH_3$ | H | H | H | $COCH_2CH=CH_2$ | O | $OCH_3$ | $OCH_3$ |
| $CH_3$ | $CH_3$ | H | H | H | $COCH_2C\equiv CH$ | O | $OCH_3$ | $OCH_3$ |
| $CH_3$ | $CH_3$ | H | H | H | $CCF_3$ | O | $OCH_3$ | $OCH_3$ |
| $CH_3$ | $CH_3$ | H | H | H | $CCH_2C(Cl)=CH_2$ | O | $OCH_3$ | $OCH_3$ |
| $CH_3$ | $CH_3$ | H | H | H | $CC\equiv CI$ | O | $OCH_3$ | $OCH_3$ |
| $CH_3$ | $CH_3$ | H | H | H | $COCF_3$ | O | $OCH_3$ | $OCH_3$ |
| $CH_3$ | $CH_3$ | H | H | H | $COCH_2CH=CHCl$ | O | $OCH_3$ | $OCH_3$ |
| $CH_3$ | $CH_3$ | H | H | H | $COCH_2C\equiv CI$ | O | $OCH_3$ | $OCH_3$ |
| $CH_3$ | $CH_3$ | H | H | H | $CCH_2OCH_3$ | O | $OCH_3$ | $OCH_3$ |
| $CH_3$ | $CH_3$ | H | H | H | $CCH_2OCH_2CH=CH_2$ | O | $OCH_3$ | $OCH_3$ |
| $CH_3$ | $CH_3$ | H | H | H | $CCH_2OCH_2C\equiv CH$ | O | $OCH_3$ | $OCH_3$ |
| $CH_3$ | $CH_3$ | H | H | H | CCN | O | $OCH_3$ | $OCH_3$ |
| $CH_3$ | $CH_3$ | H | H | H | CCHO | O | $OCH_3$ | $OCH_3$ |
| $CH_3$ | $CH_3$ | H | H | H | CCOOH | O | $OCH_3$ | $OCH_3$ |
| $CH_3$ | $CH_3$ | H | H | H | $CCOOCH_3$ | O | $OCH_3$ | $OCH_3$ |
| $CH_3$ | $CH_3$ | H | H | H | $CCOOCH_2CH=CH_2$ | O | $OCH_3$ | $OCH_3$ |
| $CH_3$ | $CH_3$ | H | H | H | $CCOOCH_2C\equiv CH$ | O | $OCH_3$ | $OCH_3$ |
| $CH_3$ | $CH_3$ | H | H | H | $CC_6H_5$ | O | $OCH_3$ | $OCH_3$ |
| $CH_3$ | $CH_3$ | H | H | H | $COC_6H_5$ | O | $OCH_3$ | $OCH_3$ |

TABLE 1-continued

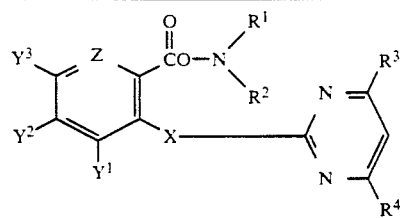

| R¹ | R² | Y¹ | Y² | Y³ | Z | X | R³ | R⁴ |
|---|---|---|---|---|---|---|---|---|
| CH₃ | CH₃ | H | H | H | CSC₆H₅ | O | OCH₃ | OCH₃ |
| CH₃ | CH₃ | H | H | H | COCH₂C₆H₅ | O | OCH₃ | OCH₃ |
| CH₃ | CH₃ | H | H | H | CSCH₂C₆H₅ | O | OCH₃ | OCH₃ |
| CH₃ | CH₃ | H | H | H | CNH₂ | O | OCH₃ | OCH₃ |
| CH₃ | CH₃ | H | H | H | CN(CH₃)₂ | O | OCH₃ | OCH₃ |
| CH₃ | CH₃ | H | H | H | CN(CH₂CH=CH₂)₂ | O | OCH₃ | OCH₃ |
| CH₃ | CH₃ | H | H | H | CN(CH₂C≡CH)₂ | O | OCH₃ | OCH₃ |
| CH₃ | CH₃ | H | H | H | CCONH₂ | O | OCH₃ | OCH₃ |
| CH₃ | CH₃ | H | H | H | CCON(C₂H₅)₂ | O | OCH₃ | OCH₃ |
| CH₃ | CH₃ | H | H | H | CCON(CH₂CH=CH₂)₂ | O | OCH₃ | OCH₃ |
| CH₃ | CH₃ | H | H | H | CCON(CH₂C≡CH)₂ | O | OCH₃ | OCH₃ |
| CH₃ | CH₃ | H | H | H | CSCH₃ | O | OCH₃ | OCH₃ |
| CH₃ | CH₃ | H | H | H | CSOC₂H₅ | O | OCH₃ | OCH₃ |
| CH₃ | CH₃ | H | H | H | CSO₂C₃H₇(n) | O | OCH₃ | OCH₃ |
| CH₃ | CH₃ | H | H | H | CSCH₂CH=CH₂ | O | OCH₃ | OCH₃ |
| CH₃ | CH₃ | H | H | H | CSCH₂C≡CH | O | OCH₃ | OCH₃ |
| CH₃ | CH₃ | H | H | H | CCH₂CH₂SCH₃ | O | OCH₃ | OCH₃ |
| CH₃ | CH₃ | H | H | H | C(CH₂)₃SOCH₃ | O | OCH₃ | OCH₃ |
| CH₃ | CH₃ | H | H | H | CCH₂SO₂CH₃ | O | OCH₃ | OCH₃ |
| CH₃ | CH₃ | H | H | H | N | O | OCH₃ | OCH₃ |
| CH₃ | CH₃ | H | H | H | CH | O | OCHF₂ | OCHF₂ |
| CH₃ | CH₃ | H | H | H | N | O | OCHF₂ | OCHF₂ |
| CH₃ | CH₃ | H | H | H | CF | O | OCHF₂ | OCHF₂ |
| CH₃ | CH₃ | H | H | H | CCl | O | OCHF₂ | OCHF₂ |
| CH₃ | C₂H₅ | H | H | H | CF | O | OCH₃ | OCH₃ |
| CH₃ | C₂H₅ | H | H | H | CCl | O | OCH₃ | OCH₃ |
| C₂H₅ | C₂H₅ | H | H | H | CF | O | OCH₃ | OCH₃ |
| C₂H₅ | C₂H₅ | H | H | H | CCl | O | OCH₃ | OCH₃ |
| C₃H₇(n) | C₃H₇(n) | H | H | H | CF | O | OCH₃ | OCH₃ |
| C₃H₇(n) | C₃H₇(n) | H | H | H | CCl | O | OCH₃ | OCH₃ |
| H | C₃H₇(i) | H | H | H | CH | O | OCH₃ | OCH₃ |
| H | C₃H₇(i) | H | H | H | N | O | OCH₃ | OCH₃ |
| H | C₃H₇(i) | H | H | H | CF | O | OCH₃ | OCH₃ |
| H | C₃H₇(i) | H | H | H | CCl | O | OCH₃ | OCH₃ |
| H | C₃H₇(i) | H | H | H | CCF₃ | O | OCH₃ | OCH₃ |
| H | C₄H₉(tert) | H | H | H | CH | O | OCH₃ | OCH₃ |
| H | C₄H₉(tert) | H | H | H | N | O | OCH₃ | OCH₃ |
| H | C₄H₉(tert) | H | H | H | CF | O | OCH₃ | OCH₃ |
| H | C₄H₉(tert) | H | H | H | CCl | O | OCH₃ | OCH₃ |
| H | C₄H₉(tert) | H | H | H | CCF₃ | O | OCH₃ | OCH₃ |
| CH₂CH=CH₂ | CH₂CH=CH₂ | H | H | H | CF | O | OCH₃ | OCH₃ |
| CH₂CH=CH₂ | CH₂CH=CH₂ | H | H | H | CCl | O | OCH₃ | OCH₃ |
| CH₂C≡CH | CH₂C≡CH | H | H | H | CF | O | OCH₃ | OCH₃ |
| CH₂C≡CH | CH₂C≡CH | H | H | H | CCl | O | OCH₃ | OCH₃ |
| CH₂CH₂Cl | CH₂CH₂Cl | H | H | H | CF | O | OCH₃ | OCH₃ |
| CH₂CH₂Cl | CH₂CH₂Cl | H | H | H | CCl | O | OCH₃ | OCH₃ |
| CH₂CH₂OCH₃ | CH₂CH₂OCH₃ | H | H | H | CF | O | OCH₃ | OCH₃ |
| CH₂CH₂OCH₃ | CH₂CH₂OCH₃ | H | H | H | CCl | O | OCH₃ | OCH₃ |
| CH₂CH₂O–CH₂CH=CH₂ | CH₂CH₂O–CH₂CH=CH₂ | H | H | H | CF | O | OCH₃ | OCH₃ |
| CH₂CH₂O–CH₂CH=CH₂ | CH₂CH₂O–CH₂CH=CH₂ | H | H | H | CCl | O | OCH₃ | OCH₃ |
| CH₂CH₂O–CH₂C≡CH | CH₂CH₂O–CH₂C≡CH | H | H | H | CF | O | OCH₃ | OCH₃ |
| CH₂CH₂O–CH₂C≡CH | CH₂CH₂O–CH₂C≡CH | H | H | H | CCl | O | OCH₃ | OCH₃ |
| CH₂COOCH₃ | CH₂COOCH₃ | H | H | H | CF | O | OCH₃ | OCH₃ |
| CH₂COOCH₃ | CH₂COOCH₃ | H | H | H | CCl | O | OCH₃ | OCH₃ |
| CH₃ | CH₂COOCH₃ | H | H | H | CF | O | OCH₃ | OCH₃ |
| CH₃ | CH₂COOCH₃ | H | H | H | CCl | O | OCH₃ | OCH₃ |
| CH₃ | CH(CH₃)COOCH₃ | H | H | H | CF | O | OCH₃ | OCH₃ |

TABLE 1-continued

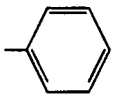

| R¹ | R² | Y¹ | Y² | Y³ | Z | X | R³ | R⁴ |
|---|---|---|---|---|---|---|---|---|
| CH₃ | CH₃CHCOOCH₃ | H | H | H | CCl | O | OCH₃ | OCH₃ |
| CH₃ | CH₂CH₂COOCH₃ | H | H | H | CF | O | OCH₃ | OCH₃ |
| CH₃ | CH₂CH₂COOCH₃ | H | H | H | CCl | O | OCH₃ | OCH₃ |
| CH₂COO−CH₂CH=CH₂ | CH₂COO−CH₂CH=CH₂ | H | H | H | CCl | O | OCH₃ | OCH₃ |
| CH₂COO−CH₂CH=CH₂ | CH₂COO−CH₂CH=CH₂ | H | H | H | CCl | O | OCH₃ | OCH₃ |
| CH₂COO−CH₂C≡CH | CH₂COO−CH₂C≡CH | H | H | H | CF | O | OCH₃ | OCH₃ |
| CH₂COO−CH₂C≡CH | CH₂COO−CH₂C≡CH | H | H | H | CCl | O | OCH₃ | OCH₃ |
| CH₂CN | CH₂CN | H | H | H | CF | O | OCH₃ | OCH₃ |
| CH₂CN | CH₂CN | H | H | H | CCl | O | OCH₃ | OCH₃ |
| CH₂CH₂CN | CH₂CH₂CN | H | H | H | CF | O | OCH₃ | OCH₃ |
| CH₂CH₂CN | CH₂CH₂CN | H | H | H | CCl | O | OCH₃ | OCH₃ |
| CH₃ | CH₂CH₂CN | H | H | H | CF | O | OCH₃ | OCH₃ |
| CH₃ | CH₂CH₂CN | H | H | H | CCl | O | OCH₃ | OCH₃ |
| CH₂CONH₂ | CH₂CONH₂ | H | H | H | CF | O | OCH₃ | OCH₃ |
| CH₂CONH₂ | CH₂CONH₂ | H | H | H | CCl | O | OCH₃ | OCH₃ |
| CH₂CON(CH₃)₂ | CH₂CON(CH₃)₂ | H | H | H | CF | O | OCH₃ | OCH₃ |
| CH₂CON(CH₃)₂ | CH₂CON(CH₃)₂ | H | H | H | CCl | O | OCH₃ | OCH₃ |
| CH₂CON(CH₂CH=CH₂)₂ | CH₂CON(CH₂CH=CH₂)₂ | H | H | H | CF | O | OCH₃ | OCH₃ |
| CH₂CON(CH₂CH=CH₂)₂ | CH₂CON(CH₂CH=CH₂)₂ | H | H | H | CCl | O | OCH₃ | OCH₃ |
| CH₂CON(CH₂C≡CH)₂ | CH₂CON(CH₂C≡CH)₂ | H | H | H | CF | O | OCH₃ | OCH₃ |
| CH₂CON(CH₂C≡CH)₂ | CH₂CON(CH₂C≡CH)₂ | H | H | H | CCl | O | OCH₃ | OCH₃ |
| CH₃ | CH₂CH₂CONH₂ | H | H | H | CF | O | OCH₃ | OCH₃ |
| CH₃ | CH₂CH₂CONH₂ | H | H | H | CCl | O | OCH₃ | OCH₃ |
| CH₂CH₂SCH₃ | CH₂CH₂SCH₃ | H | H | H | CF | O | OCH₃ | OCH₃ |
| CH₂CH₂SCH₃ | CH₂CH₂SCH₃ | H | H | H | CCl | O | OCH₃ | OCH₃ |
| CH₂CH₂SOCH₃ | CH₂CH₂SOCH₃ | H | H | H | CF | O | OCH₃ | OCH₃ |
| CH₂CH₂SOCH₃ | CH₂CH₂SOCH₃ | H | H | H | CCl | O | OCH₃ | OCH₃ |
| CH₂CH₂SO₂CH₃ | CH₂CH₂SO₂CH₃ | H | H | H | CF | O | OCH₃ | OCH₃ |
| CH₂CH₂SO₂CH₃ | CH₂CH₂SO₂CH₃ | H | H | H | CCl | O | OCH₃ | OCH₃ |
| H | cyclohexyl | H | H | H | CH | O | OCH₃ | OCH₃ |
| H | cyclohexyl | H | H | H | N | O | OCH₃ | OCH₃ |
| H | cyclohexyl | H | H | H | CF | O | OCH₃ | OCH₃ |
| H | cyclohexyl | H | H | H | CCl | O | OCH₃ | OCH₃ |
| H | cyclohexyl | H | H | H | CCF₃ | O | OCH₃ | OCH₃ |
| H | phenyl | H | H | H | CCl | O | OCH₃ | OCH₃ |

TABLE 1-continued

[Structure: Y³, Z, C(=O)-N(R¹)(R²), with attached ring containing X linked to pyrimidine bearing R³ and R⁴; Y¹, Y² on the other ring]

| R¹ | R² | Y¹ | Y² | Y³ | Z | X | R³ | R⁴ |
|---|---|---|---|---|---|---|---|---|
| H | 2-CH₃-phenyl | H | H | H | CCl | O | OCH₃ | OCH₃ |
| H | 3-OCH₃-phenyl | H | H | H | CCl | O | OCH₃ | OCH₃ |
| CH₃ | 4-Cl-phenyl | H | H | H | CCl | O | OCH₃ | OCH₃ |
| CH₃ | 2-COOCH₃-phenyl | H | H | H | CCl | O | OCH₃ | OCH₃ |
| CH₃ | 3-CF₃-phenyl | H | H | H | CCl | O | OCH₃ | OCH₃ |
| phenyl | phenyl | H | H | H | CCl | O | OCH₃ | OCH₃ |
| benzyl | benzyl | H | H | H | CH | O | OCH₃ | OCH₃ |
| benzyl | benzyl | H | H | H | N | O | OCH₃ | OCH₃ |
| benzyl | benzyl | H | H | H | CF | O | OCH₃ | OCH₃ |
| benzyl | benzyl | H | H | H | CCl | O | OCH₃ | OCH₃ |
| benzyl | benzyl | H | H | H | CCF₃ | O | OCH₃ | OCH₃ |

TABLE 1-continued

| R¹ | R² | Y¹ | Y² | Y³ | Z | X | R³ | R⁴ |
|---|---|---|---|---|---|---|---|---|
| | ←CH₂→₄ | H | H | H | CF | O | OCH₃ | OCH₃ |
| | ←CH₂→₄ | H | H | H | CCl | O | OCH₃ | OCH₃ |
| | ←CH₂→₅ | H | H | H | CH | O | OCH₃ | OCH₃ |
| | ←CH₂→₅ | H | H | H | N | O | OCH₃ | OCH₃ |
| | ←CH₂→₅ | H | H | H | CF | O | OCH₃ | OCH₃ |
| | ←CH₂→₅ | H | H | H | CCl | O | OCH₃ | OCH₃ |
| | ←CH₂→₅ | H | H | H | CCF₃ | O | OCH₃ | OCH₃ |
| | ←CH₂→₆ | H | H | H | CF | O | OCH₃ | OCH₃ |
| | ←CH₂→₆ | H | H | H | CCl | O | OCH₃ | OCH₃ |
| | $-\text{CH(CH}_3\text{)CH}_2\text{CH}_2\text{CH(CH}_3\text{)}-$ | H | H | H | CH | O | OCH₃ | OCH₃ |
| | $-\text{CH(CH}_3\text{)CH}_2\text{CH}_2\text{CH(CH}_3\text{)}-$ | H | H | H | N | O | OCH₃ | OCH₃ |
| | $-\text{CH(CH}_3\text{)CH}_2\text{CH}_2\text{CH(CH}_3\text{)}-$ | H | H | H | CF | O | OCH₃ | OCH₃ |
| | $-\text{CH(CH}_3\text{)CH}_2\text{CH}_2\text{CH(CH}_3\text{)}-$ | H | H | H | CCl | O | OCH₃ | OCH₃ |
| | $-\text{CH(CH}_3\text{)CH}_2\text{CH}_2\text{CH}_2\text{CH(CH}_3\text{)}-$ | H | H | H | CF | O | OCH₃ | OCH₃ |
| | $-\text{CH(CH}_3\text{)CH}_2\text{CH}_2\text{CH}_2\text{CH(CH}_3\text{)}-$ | H | H | H | CCl | O | OCH₃ | OCH₃ |
| | $-\text{CH(CH}_3\text{)CH}_2\text{CH}_2\text{CH}_2\text{CH(CH}_3\text{)}-$ | H | H | H | CCF₃ | O | OCH₃ | OCH₃ |
| | $-\text{CH}_2\text{CH(CH}_3\text{)CH}_2\text{CH}_2\text{CH}_2-$ | H | H | H | CCl | O | OCH₃ | OCH₃ |
| | $-\text{CH(CH}_3\text{)CH}_2\text{CH}_2\text{CH}_2\text{CH}_2-$ | H | H | H | CCl | OCH₃ | OCH₃ | |
| | —CH₂CH₂—O—CH₂CH₂— | H | H | H | CF | O | OCH₃ | OCH₃ |
| | —CH₂CH₂—O—CH₂CH₂— | H | H | H | CCl | O | OCH₃ | OCH₃ |
| | $-\text{CH}_2\text{CH(CH}_3\text{)}-\text{O}-\text{CH(CH}_3\text{)CH}_2-$ | H | H | H | CCl | O | OCH₃ | OCH₃ |
| CH₃ | C₂H₅ | H | H | H | CH | O | OCH₃ | OCH₃ |
| CH₃ | C₂H₅ | H | H | H | N | O | OCH₃ | OCH₃ |
| CH₃ | C₂H₅ | H | H | H | CCF₃ | O | OCH₃ | OCH₃ |
| C₂H₅ | C₂H₅ | H | H | H | CH | O | OCH₃ | OCH₃ |
| C₂H₅ | C₂H₅ | H | H | H | N | O | OCH₃ | OCH₃ |
| C₂H₅ | C₂H₅ | H | H | H | CCF₃ | O | OCH₃ | OCH₃ |
| C₃H₇(n) | C₃H₇(n) | H | H | H | CH | O | OCH₃ | OCH₃ |
| C₃H₇(n) | C₃H₇(n) | H | H | H | N | O | OCH₃ | OCH₃ |
| C₃H₇(n) | C₃H₇(n) | H | H | H | CCF₃ | O | OCH₃ | OCH₃ |
| | —CH₂CH₂—O—CH₂CH₂— | H | H | H | CH | O | OCH₃ | OCH₃ |
| | —CH₂CH₂—O—CH₂CH₂— | H | H | H | N | O | OCH₃ | OCH₃ |
| | $-\text{CH(CH}_3\text{)CH}_2\text{CH}_2\text{CH(CH}_3\text{)}-$ | H | H | H | CH | O | OCH₃ | OCH₃ |

TABLE 1-continued

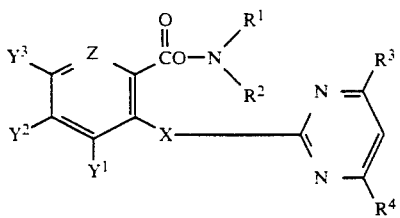

| R¹ | R² | Y¹ | Y² | Y³ | Z | X | R³ | R⁴ |
|---|---|---|---|---|---|---|---|---|
| | CH₃     CH₃<br>–CHCH₂CH₂CH₂CH– | H | H | H | N | O | OCH₃ | OCH₃ |
| | –CH₂CH₂CH₂CH₂– | H | H | H | CH | O | OCH₃ | OCH₃ |
| | –CH₂CH₂CH₂CH₂– | H | H | H | N | O | OCH₃ | OCH₃ |
| | –CH₂CH₂CH₂CH₂– | H | H | H | CCF₃ | O | OCH₃ | OCH₃ |
| | CH₃     C₂H₅<br>–CHCH₂CH₂CH– | H | H | H | CF | O | OCH₃ | OCH₃ |
| | CH₃     C₂H₅<br>–CHCH₂CH₂CH– | H | H | H | CCl | O | OCH₃ | OCH₃ |
| | C₂H₅     C₂H₅<br>–CHCH₂CH₂CH₂CH– | H | H | H | CF | O | OCH₃ | OCH₃ |
| | C₂H₅     C₂H₅<br>–CHCH₂CH₂CH₂CH– | H | H | H | CCl | O | OCH₃ | OCH₃ |
| | C₃H₇(n)<br>–CH₂CHCH₂CH₂CH₂– | H | H | H | CF | O | OCH₃ | OCH₃ |
| | C₃H₇(n)<br>–CH₂CHCH₂CH₂CH₂– | H | H | H | CCl | O | OCH₃ | OCH₃ |
| | OCH₃<br>–CH₂CH₂CHCH₂CH₂– | H | H | H | CF | O | OCH₃ | OCH₃ |
| | OCH₃<br>–CH₂CH₂CHCH₂CH₂– | H | H | H | CCl | O | OCH₃ | OCH₃ |
| | Cl<br>–CH₂CH₂CHCH₂CH₂– | H | H | H | CF | O | OCH₃ | OCH₃ |
| | Cl<br>–CH₂CH₂CHCH₂CH₂– | H | H | H | CCl | O | OCH₃ | OCH₃ |
| | –CH₂CH₂SO₂CH₂CH₂– | H | H | H | CCl | O | OCH₃ | OCH₃ |

In producing the present compounds, when the phenol derivative (a starting compound of compound (I)), represented by the formula (II) is other than those in which Y⁴ is a group,

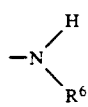

(in which R⁶ is as defined above) or a group,

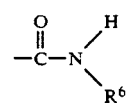

(in which R⁶ is as defined above), said phenol derivative can be produced by reacting an aromatic carboxylic acid halide derivative represented by the following formula (VII) with the hydroxylamine derivative represented by the formula (V) in the presence of a dehydrohalogenating agent and then hydrolyzing the resulting compound with a base (e.g. sodium hydroxide, potassium hydroxide) or an acid (e.g. hydrochloric acid, sulfuric acid) to remove the group,

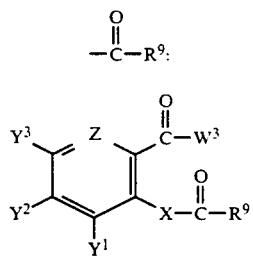

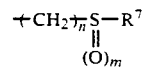

(in which $R^7$, m and n are as defined above), or a group represented by the formula,

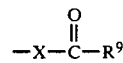

(in which $R^9$ and X are as defined as defined above).

The dehydrohalogenating agent includes pyridine, triethylamine, N,N-diethylaniline, etc.

After completion of the reaction, the reaction solution is after-treated as usual. That is, water is added to the solution which is then extracted with an organic solvent and concentrated, and if necessary, the product obtained is subjected to the chromatography, distillation, recrystallization, etc. Thus, the phenol derivative (II) can be obtained.

The phenol derivative represented by the formula (II) can also be produced by reacting [reaction (iii)] an aromatic carboxylic acid derivative represented by the formula (VIII),

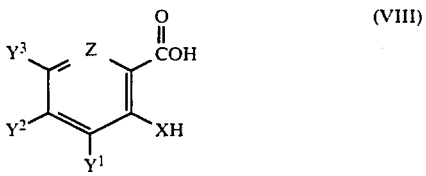

(wherein X, $Y^1$, $Y^2$, $Y^3$ and Z are as defined above), with an acid-halogenating agent or an active esterifying agent, and subsequently reacting [reaction (iv)] the resulting reaction product with the hydroxylamine derivative represented by the formula (V).

The above reactions (iii) and (iv) are carried out according to the foregoing reactions (i) and (ii), respectively. The aromatic carboxylic acid halide derivative (VII) can be produced according to Beilstein H10/p.86, EI10/p.43, EII10/p.55, EIII10/p.151, EIV10/p.169, etc.

The aromatic carboxylic acid derivative (VIII) can be produced according to J. Org. Chem., 27, 3551 (1962), Chem. Pharm. Bull., 31, 407 (1983), Yakugaku Zasshi, 99, 657 (1979), Chem. Pharm. Bull., 27, 1468 (1979), J. Med. Chem., 21, 1093 (1978), Yakugaku Zasshi, 92, 1386 (1972), Eur. J. Med. Chem–Chim. Ther., 21, 379 (1986), J. Chem. Soc., Perkin Trans. 1, 2069 (1979), J. Chem. Soc., Perkin Trans. 1, 2079 (1979), J. Chem. Soc., Chem. Commun., 1127 (1968), J. Med. Chem., 31, 1039 (1988), Indian J. Chem., 25B, 796 (1986), J. Am. Chem. Soc., 107, 4593 (1985), J. Org. Chem., 50, 718 (1985), J. Agric. Food Chem., 32, 747 (1984), J. Pharm. Pharmacol., 35, 718 (1983), J. Org. Chem., 48, 1935 (1983), J. Chem. Soc., Chem. commun., 1974, 362, etc.

The hydroxylamine derivatives [V] can be produced according to Beilstein H/P.533, E II/p. 952, E III/p. 1713, E IV/p. 3299, Chem. Ber., 35, 703 (1902), Chem. Ber., 33, 3387 1900), Chem. Ber., 34, 738 (1901), Chem. Ber., 62, 2458 (1929), J. Am. Chem. Soc., 76, 2984 (1954), J. Org. Chem., 25, 621 (1960), Chem. Ber., 56, 1856 (1923), Chem. Ber., 58, 2430 (1925), J. Org. Chem., wherein X, $Y^1$, $Y^2$ and $Y^3$ are as defined above, $W^3$ represents a halogen atom, $R^9$ represents a $C_1$–$C_6$ alkyl group, and Z represents $CY^{4'}$ wherein $Y^{4'}$ represents a hydrogen atom, a nitro group, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_3$–$C_6$ alkenyloxy group, a $C_3$–$C_6$ alkynyloxy group, a halo $C_1$–$C_6$ alkyl group, a halo $C_2$–$C_6$ alkenyl group, a halo $C_2$–$C_6$ alkynyl group, a halo $C_1$–$C_6$ alkoxy group, a halo $C_3$–$C_6$ alkenyloxy group, a halo $C_3$–$C_6$ alkynyloxy group, a $C_1$–$C_6$ alkoxy $C_1$–$C_6$ alkyl group, a $C_3$–$C_6$ alkenyloxy $C_1$–$C_6$ alkyl group, a $C_3$–$C_6$ alkynyloxy $C_1$–$C_6$ alkyl group, a cyano group, a formyl group, a carboxyl group, a $C_1$–$C_6$ alkoxycarbonyl group, a $C_3$–$C_6$ alkenyloxycarbonyl group, a $C_3$–$C_6$ alkynyloxycarbonyl group; a phenyl, phenoxy, phenylthio, benzyloxy or benzylthio group which being optionally substituted with a $C_1$–$C_6$ alkyl group, a $C_1$–$C_6$ alkoxy group, a halo $C_1$–$C_6$ alkyl group, a $C_1$–$C_6$ alkoxycarbonyl group or a halogen atom; and a group represented by the formula,

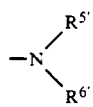

(in which each of $R^{5'}$ and $R^{6'}$, which may be the same or different, represents a $C_1$–$C_6$ alkyl group, a $C_3$–$C_6$ alkenyl group or a $C_3$–$C_6$ alkynyl group), a group represented by the formula

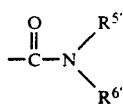

(in which $R^{4'}$ and $R^{6'}$ are as defined above), a group represented by the formula,

(in which $R^7$ and m are as defined above), a group represented by the formula,

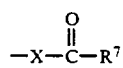

(in which R; and X are as defined above, a group represented by the formula, 28, 265 (1963), Org. Synth. Coll. Vol. III, p. 668, Chem. Ber., 36, 2700 (1903), Chem. Ber., 42, 2306 (1909), J. Am. Chem. Soc., 83, 1374 (1961), Chem. Ber., 71, 2247 (1938), Chem. Ber., 41, 1936 (1908), Synth. Commun., 19, 3509 (1989), J. Org. Chem., 55, 1981 (1990), Synthesis, 1977, 856, Org. Synth. Coll. Vol. IV, p. 612.

Table 2 illustrates examples of the compound (II) which can be produced by the above procedures. Compound (I) and Compound (II) includes their stereo isomers having herbicidal activity.

TABLE 2

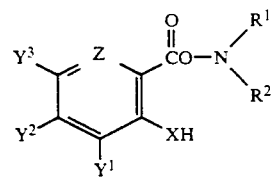

| $R^1$ | $R^2$ | $Y^1$ | $Y^2$ | $Y^3$ | Z | X |
|---|---|---|---|---|---|---|
| H | H | H | H | H | CH | O |
| H | H | H | H | H | N | O |
| H | H | H | H | H | CCl | O |
| H | H | H | H | H | CF | O |
| H | $CH_3$ | H | H | H | CH | O |
| H | $CH_3$ | H | H | H | N | O |
| H | $CH_3$ | H | H | H | CCl | O |
| H | $CH_3$ | H | H | H | CF | O |
| $CH_3$ | $CH_3$ | H | H | H | CH | O |
| $CH_3$ | $CH_3$ | H | H | H | CH | S |
| $CH_3$ | $CH_3$ | H | H | H | CH | O |
| $CH_3$ | $CH_3$ | $CH_3$ | H | H | CH | O |
| $CH_3$ | $CH_3$ | H | $CH_3$ | H | CH | O |
| $CH_3$ | $CH_3$ | H | H | $CH_3$ | CH | O |
| $CH_3$ | $CH_3$ | H | H | H | $CCH_3$ | O |
| $CH_3$ | $CH_3$ | H | H | H | $CC_2H_5$ | O |
| $CH_3$ | $CH_3$ | $OCH_3$ | H | H | CH | O |
| $CH_3$ | $CH_3$ | H | $OCH_3$ | H | CH | O |
| $CH_3$ | $CH_3$ | H | H | $OCH_3$ | CH | O |
| $CH_3$ | $CH_3$ | H | H | H | $COCH_3$ | O |
| $CH_3$ | $CH_3$ | F | H | H | CH | O |
| $CH_3$ | $CH_3$ | H | F | H | CH | O |
| $CH_3$ | $CH_3$ | H | H | F | CH | O |
| $CH_3$ | $CH_3$ | H | H | H | CF | O |
| $CH_3$ | $CH_3$ | H | H | F | CF | O |
| $CH_3$ | $CH_3$ | F | H | H | CF | O |
| $CH_3$ | $CH_3$ | F | H | F | CF | O |
| $CH_3$ | $CH_3$ | Cl | H | H | CH | O |
| $CH_3$ | $CH_3$ | H | Cl | H | CH | O |
| $CH_3$ | $CH_3$ | H | H | Cl | CH | O |
| $CH_3$ | $CH_3$ | H | H | H | CCl | O |
| $CH_3$ | $CH_3$ | H | H | F | CCl | O |
| $CH_3$ | $CH_3$ | H | H | H | CBr | O |
| $CH_3$ | $CH_3$ | H | H | H | CI | O |
| $CH_3$ | $CH_3$ | H | H | H | COH | O |
| $CH_3$ | $CH_3$ | H | H | H | CSH | O |
| $CH_3$ | $CH_3$ | H | H | H | $CNO_2$ | O |
| $CH_3$ | $CH_3$ | H | H | H | $CCH=CH_2$ | O |
| $CH_3$ | $CH_3$ | H | H | H | $CC\equiv CH$ | O |
| $CH_3$ | $CH_3$ | H | H | H | $COC_2H_5$ | O |
| $CH_3$ | $CH_3$ | H | H | H | $COCH_2CH=CH_2$ | O |
| $CH_3$ | $CH_3$ | H | H | H | $COCH_2C\equiv CH$ | O |
| $CH_3$ | $CH_3$ | H | H | H | $CCF_3$ | O |
| $CH_3$ | $CH_3$ | H | H | H | $CCH_2C(Cl)=CH_2$ | O |
| $CH_3$ | $CH_3$ | H | H | H | $CC\equiv CI$ | O |
| $CH_3$ | $CH_3$ | H | H | H | $COCF_3$ | O |
| $CH_3$ | $CH_3$ | H | H | H | $COCH_2CH=CHCl$ | O |
| $CH_3$ | $CH_3$ | H | H | H | $COCH_2C\equiv CI$ | O |
| $CH_3$ | $CH_3$ | H | H | H | $CCH_2OCH_3$ | O |
| $CH_3$ | $CH_3$ | H | H | H | $CCH_2OCH_2CH=CH_2$ | O |
| $CH_3$ | $CH_3$ | H | H | H | $CCH_2OCH_2C\equiv CH$ | O |
| $CH_3$ | $CH_3$ | H | H | H | CCN | O |
| $CH_3$ | $CH_3$ | H | H | H | CCHO | O |
| $CH_3$ | $CH_3$ | H | H | H | CCOOH | O |
| $CH_3$ | $CH_3$ | H | H | H | $CCOOCH_3$ | O |
| $CH_3$ | $CH_3$ | H | H | H | $CCOOCH_2CH=CH_2$ | O |
| $CH_3$ | $CH_3$ | H | H | H | $CCOOCH_2C\equiv CH$ | O |
| $CH_3$ | $CH_3$ | H | H | H | $CC_6H_5$ | O |
| $CH_3$ | $CH_3$ | H | H | H | $COC_6H_5$ | O |
| $CH_3$ | $CH_3$ | H | H | H | $CSC_6H_5$ | O |
| $CH_3$ | $CH_3$ | H | H | H | $COCH_2C_6H_5$ | O |
| $CH_3$ | $CH_3$ | H | H | H | $CSCH_2C_6H_5$ | O |
| $CH_3$ | $CH_3$ | H | H | H | $CNH_2$ | O |
| $CH_3$ | $CH_3$ | H | H | H | $CN(CH_3)_2$ | O |

TABLE 2-continued

Structure: Y³–Z=... Y²–...=Y¹, with CO-N(R¹)(R²) and XH group on the ring.

| R¹ | R² | Y¹ | Y² | Y³ | Z | X |
|---|---|---|---|---|---|---|
| CH₃ | CH₃ | H | H | H | CN(CH₂CH=CH₂)₂ | O |
| CH₃ | CH₃ | H | H | H | CN(CH₂C≡CH)₂ | O |
| CH₃ | CH₃ | H | H | H | CCONH₂ | O |
| CH₃ | CH₃ | H | H | H | CCON(C₂H₅)₂ | O |
| CH₃ | CH₃ | H | H | H | CCON(CH₂CH=CH₂)₂ | O |
| CH₃ | CH₃ | H | H | H | CCON(CH₂C≡CH)₂ | O |
| CH₃ | CH₃ | H | H | H | CSCH₃ | O |
| CH₃ | CH₃ | H | H | H | CSOC₂H₅ | O |
| CH₃ | CH₃ | H | H | H | CSO₂C₃H₇(n) | O |
| CH₃ | CH₃ | H | H | H | CSCH₂CH=CH₂ | O |
| CH₃ | CH₃ | H | H | H | CSCH₂C≡CH | O |
| CH₃ | CH₃ | H | H | H | CCH₂CH₂SCH₃ | O |
| CH₃ | CH₃ | H | H | H | C(CH₂)₃SOCH₃ | O |
| CH₃ | CH₃ | H | H | H | CCH₂SO₂CH₃ | O |
| CH₃ | CH₃ | H | H | H | N | O |
| CH₃ | C₂H₅ | H | H | H | CF | O |
| CH₃ | C₂H₅ | H | H | H | CCl | O |
| C₂H₅ | C₂H₅ | H | H | H | CF | O |
| C₂H₅ | C₂H₅ | H | H | H | CCl | O |
| C₃H₇(n) | C₃H₇(n) | H | H | H | CF | O |
| C₃H₇(n) | C₃H₇(n) | H | H | H | CCl | O |
| H | C₃H₇(i) | H | H | H | CH | O |
| H | C₃H₇(i) | H | H | H | N | O |
| H | C₃H₇(i) | H | H | H | CF | O |
| H | C₃H₇(i) | H | H | H | CCl | O |
| H | C₃H₇(i) | H | H | H | CCF₃ | O |
| H | C₄H₉(tert) | H | H | H | CH | O |
| H | C₄H₉(tert) | H | H | H | N | O |
| H | C₄H₉(tert) | H | H | H | CF | O |
| H | C₄H₉(tert) | H | H | H | CCl | O |
| H | C₄H₉(tert) | H | H | H | CCF₃ | O |
| CH₂CH=CH₂ | CH₂CH=CH₂ | H | H | H | CF | O |
| CH₂CH=CH₂ | CH₂CH=CH₂ | H | H | H | CCl | O |
| CH₂C≡CH | CH₂C≡CH | H | H | H | CF | O |
| CH₂C≡CH | CH₂C≡CH | H | H | H | CCl | O |
| CH₂CH₂Cl | CH₂CH₂Cl | H | H | H | CF | O |
| CH₂CH₂Cl | CH₂CH₂Cl | H | H | H | CCl | O |
| CH₂CH₂OCH₃ | CH₂CH₂OCH₃ | H | H | H | CF | O |
| CH₂CH₂OCH₃ | CH₂CH₂OCH₃ | H | H | H | CCl | O |
| CH₂CH₂O-CH₂CH=CH₂ | CH₂CH₂O-CH₂CH=CH₂ | H | H | H | CF | O |
| CH₂CH₂O-CH₂CH=CH₂ | CH₂CH₂O-CH₂CH=CH₂ | H | H | H | CCl | O |
| CH₂CH₂O-CH₂C≡CH | CH₂CH₂O-CH₂C≡CH | H | H | H | CF | O |
| CH₂CH₂O-CH₂C≡CH | CH₂CH₂O-CH₂C≡CH | H | H | H | CCl | O |
| CH₂COOCH₃ | CH₂COOCH₃ | H | H | H | CF | O |
| CH₂COOCH₃ | CH₂COOCH₃ | H | H | H | CCl | O |
| CH₃ | CH₂COOCH₃ | H | H | H | CF | O |
| CH₃ | CH₂COOCH₃ | H | H | H | CCl | O |
| CH₃ | CH(CH₃)COOCH₃ | H | H | H | CF | O |
| CH₃ | CH(CH₃)COOCH₃ | H | H | H | CCl | O |
| CH₃ | CH₂CH₂COOCH₃ | H | H | H | CF | O |
| CH₃ | CH₂CH₂COOCH₃ | H | H | H | CCl | O |
| CH₂COO-CH₂CH=CH₂ | CH₂COO-CH₂CH=CH₂ | H | H | H | CCl | O |

TABLE 2-continued

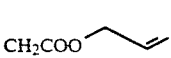

| R¹ | R² | Y¹ | Y² | Y³ | Z | X |
|---|---|---|---|---|---|---|
| CH₂COO-CH₂CH=CH₂ | CH₂COO-CH₂CH=CH₂ | H | H | H | CCl | O |
| CH₂COO-CH₂C≡CH | CH₂COO-CH₂C≡CH | H | H | H | CF | O |
| CH₂COO-CH₂C≡CH | CH₂COO-CH₂C≡CH | H | H | H | CCl | O |
| CH₂CN | CH₂CN | H | H | H | CF | O |
| CH₂CN | CH₂CN | H | H | H | CCl | O |
| CH₂CH₂CN | CH₂CH₂CN | H | H | H | CF | O |
| CH₂CH₂CN | CH₂CH₂CN | H | H | H | CCl | O |
| CH₃ | CH₂CH₂CN | H | H | H | CF | O |
| CH₃ | CH₂CH₂CN | H | H | H | CCl | O |
| CH₂CONH₂ | CH₂CONH₂ | H | H | H | CF | O |
| CH₂CONH₂ | CH₂CONH₂ | H | H | H | CCl | O |
| CH₂CON(CH₃)₂ | CH₂CON(CH₃)₂ | H | H | H | CF | O |
| CH₂CON(CH₃)₂ | CH₂CON(CH₃)₂ | H | H | H | CCl | O |
| CH₂CON(CH₂CH=CH₂)₂ | CH₂CON(CH₂CH=CH₂)₂ | H | H | H | CF | O |
| CH₂CON(CH₂CH=CH₂)₂ | CH₂CON(CH₂CH=CH₂)₂ | H | H | H | CCl | O |
| CH₂CON(CH₂C≡CH)₂ | CH₂CON(CH₂C≡CH)₂ | H | H | H | CF | O |
| CH₂CON(CH₂C≡CH)₂ | CH₂CON(CH₂C≡CH)₂ | H | H | H | CCl | O |
| CH₃ | CH₂CH₂CONH₂ | H | H | H | CF | O |
| CH₃ | CH₂CH₂CONH₂ | H | H | H | CCl | O |
| CH₂CH₂SCH₃ | CH₂CH₂SCH₃ | H | H | H | CF | O |
| CH₂CH₂SCH₃ | CH₂CH₂SCH₃ | H | H | H | CCl | O |
| CH₂CH₂SOCH₃ | CH₂CH₂SOCH₃ | H | H | H | CF | O |
| CH₂CH₂SOCH₃ | CH₂CH₂SOCH₃ | H | H | H | Cl | O |
| CH₂CH₂SO₂CH₃ | CH₂CH₂SO₂CH₃ | H | H | H | CF | O |
| CH₂CH₂SO₂CH₃ | CH₂CH₂SO₂CH₃ | H | H | H | CCl | O |
| H | cyclohexyl | H | H | H | CH | O |
| H | cyclohexyl | H | H | H | N | O |
| H | cyclohexyl | H | H | H | CF | O |
| H | cyclohexyl | H | H | H | CCl | O |
| H | cyclohexyl | H | H | H | CCF₃ | O |
| H | phenyl | H | H | H | CCl | O |
| H | 2-methylphenyl | H | H | H | CCl | O |
| H | 3-methoxyphenyl | H | H | H | CCl | O |

TABLE 2-continued

| R¹ | R² | Y¹ | Y² | Y³ | Z | X |
|---|---|---|---|---|---|---|
| CH₃ | 4-Cl-C₆H₄- | H | H | H | CCl | O |
| CH₃ | 2-(COOCH₃)-C₆H₄- | H | H | H | CCl | O |
| CH₃ | 3-(CF₃)-C₆H₄- | H | H | H | CCl | O |
| C₆H₅- | C₆H₅- | H | H | H | CCl | O |
| C₆H₅CH₂- | C₆H₅CH₂- | H | H | H | CH | O |
| C₆H₅CH₂- | C₆H₅CH₂- | H | H | H | N | O |
| C₆H₅CH₂- | C₆H₅CH₂- | H | H | H | CF | O |
| C₆H₅CH₂- | C₆H₅CH₂- | H | H | H | CCl | O |
| C₆H₅CH₂- | C₆H₅CH₂- | H | H | H | CCF₃ | O |
| | -(CH₂)₄- | H | H | H | CF | O |
| | -(CH₂)₄- | H | H | H | CCl | O |
| | -(CH₂)₅- | H | H | H | CH | O |
| | -(CH₂)₅- | H | H | H | N | O |
| | -(CH₂)₅- | H | H | H | CF | O |
| | -(CH₂)₅- | H | H | H | CCl | O |
| | -(CH₂)₅- | H | H | H | CCF₃ | O |
| | -(CH₂)₆- | H | H | H | CF | O |
| | -(CH₂)₆- | H | H | H | CCl | O |
| | -CH(CH₃)CH₂CH₂CH(CH₃)- | H | H | H | CH | O |

TABLE 2-continued

| R¹ | R² | Y¹ | Y² | Y³ | Z | X |
|---|---|---|---|---|---|---|
| —CH(CH₃)CH₂CH₂CH(CH₃)— | | H | H | H | N | O |
| —CH(CH₃)CH₂CH₂CH(CH₃)— | | H | H | H | CF | O |
| —CH(CH₃)CH₂CH₂CH(CH₃)— | | H | H | H | CCl | O |
| —CH(CH₃)CH₂CH₂CH₂CH(CH₃)— | | H | H | H | CF | O |
| —CH(CH₃)CH₂CH₂CH₂CH(CH₃)— | | H | H | H | CCl | O |
| —CH(CH₃)CH₂CH₂CH₂CH(CH₃)— | | H | H | H | CCF₃ | O |
| —CH₂CH(CH₃)CH₂CH₂CH₂— | | H | H | H | CCl | O |
| —CH(CH₃)CH₂CH₂CH₂CH₂— | | H | H | H | CCl | O |
| —CH₂CH₂—O—CH₂CH₂— | | H | H | H | CF | O |
| —CH₂CH₂—O—CH₂CH₂— | | H | H | H | CCl | O |
| —CH₂CH(CH₃)—O—CH(CH₃)CH₂— | | H | H | H | CCl | O |
| CH₃ | C₂H₅ | H | H | H | CH | O |
| CH₃ | C₂H₅ | H | H | H | N | O |
| CH₃ | C₂H₅ | H | H | H | CCF₃ | O |
| C₂H₅ | C₂H₅ | H | H | H | CH | O |
| C₂H₅ | C₂H₅ | H | H | H | N | O |
| C₂H₅ | C₂H₅ | H | H | H | CCF₃ | O |
| C₃H₇(n) | C₃H₇(n) | H | H | H | CH | O |
| C₃H₇(n) | C₃H₇(n) | H | H | H | N | O |
| C₃H₇(n) | C₃H₇(n) | H | H | H | CCF₃ | O |
| —CH₂CH₂—O—CH₂CH₂— | | H | H | H | CH | O |
| —CH₂CH₂—O—CH₂CH₂— | | H | H | H | N | O |
| —CH(CH₃)CH₂CH₂CH(CH₃)— | | H | H | H | CH | O |
| —CH(CH₃)CH₂CH₂CH(CH₃)— | | H | H | H | N | O |
| —CH₂CH₂CH₂CH₂— | | H | H | H | CH | O |
| —CH₂CH₂CH₂CH₂— | | H | H | H | N | O |
| —CH₂CH₂CH₂CH₂— | | H | H | H | CCF₃ | O |
| —CH(CH₃)CH₂CH₂CH(C₂H₅)— | | H | H | H | CF | O |
| —CH(CH₃)CH₂CH₂CH(C₂H₅)— | | H | H | H | CCl | O |

TABLE 2-continued $$Y^3\underset{Y^2}{\overset{Z}{\diagup}}\underset{Y^1}{\overset{}{\diagdown}}\underset{XH}{\overset{CO-N\diagup R^1}{\diagdown R^2}}$$

| R¹ | R² | Y¹ | Y² | Y³ | Z | X |
|---|---|---|---|---|---|---|
| | C₂H₅   C₂H₅<br> \|        \|<br>—CHCH₂CH₂CH₂CH— | H | H | H | CF | O |
| | C₂H₅   C₂H₅<br> \|        \|<br>—CHCH₂CH₂CH₂CH— | H | H | H | CCl | O |
| | C₃H₇(n)<br>\|<br>—CH₂CHCH₂CH₂CH₂— | H | H | H | CF | O |
| | C₃H₇(n)<br>\|<br>—CH₂CHCH₂CH₂CH₂— | H | H | H | CCl | O |
| | OCH₃<br>\|<br>—CH₂CH₂CHCH₂CH₂— | H | H | H | CF | O |
| | OCH₃<br>\|<br>—CH₂CH₂CHCH₂CH₂— | H | H | H | CCl | O |
| | Cl<br>\|<br>—CH₂CH₂CHCH₂CH₂— | H | H | H | CF | O |
| | Cl<br>\|<br>—CH₂CH₂CHCH₂CH₂— | H | H | H | CCl | O |
| | —CH₂CH₂SO₂CH₂CH₂— | H | H | H | CCl | O |

The present compound (I) has an excellent herbicidal activity and some of them have excellent selectivity between crops and weeds.

That is, the present compound, when used for foliar treatment and soil treatment in upland fields, exhibits a herbicidal activity against various weeds in question. Also, the present compound (I), when used for flooding treatment in paddy fields, exhibits a herbicidal activity against various weeds in question.

The present compound (I) can control a wide range of weeds generated in crop lands or non-crop lands, can be applied in low dosage rates, has a broad herbicidal spectrum and also can safely be used for no-till cultivation in soybean fields, peanut fields, corn fields, etc.

As weeds which can be controlled by the present compound, there are mentioned for example broadleaved weeds such as wild buckwheat (*Polyqonum convolvulus*), pale smartweed (*Polyqonum lapathifolium*), common purslane (*Portulaca oleracea*), chickweed (*Stellaria media*), common lambsquarters (*Chenopodium album*), redroot pigweed (*Amaranthus retroflexus*), radish (*Raphanus sativus*), wild mustard (*Sinapis arvensis*), shepherds purse (*Capsella bursa-pastoris*), hemp sesbania (*sesbania exaltata*), sicklepod (*Cassia obtusifolia*), velvetleaf (*Abutilon theophrasti*), prickly sida (*Sida spinosa*), field pansy (*Viola arvensis*), cleavers (*Galium aparine*), ivyleaf morningglory (*Ipomoea hederacea*), tall morningglory (*Ipomoea purpurea*), field bindweed (*Convolvulus arvensis*), red deadnettle (*Lamium purpureum*), henbit (*Lamium amplexicaure*), jimsonweed (*Datura stramonium*), black nightshade (*Solanum niqrum*), birdseye speedwell (*Veronica persica*), cocklebur (*Xanthium strumarium*), sunflower (*Helianthus annuus*), scentless chamomile (*Matricaria perforata*), corn marigold (*Chrysanthemum segetum*), etc.; Gramineae weeds such as Japanese millet (*Echinochloa frumentacea*), barnyardgrass (*Echinochloa crus-galli*), green foxtail (*Setaria viridis*), large crabgrass (*Digitaria sanquinalis*), annual bluegrass (*Poa annua*), blackgrass (*Alopecurus myosuroides*), oat (*Avena sativa*), wild oat (*Avena fatua*), johnsongrass (*Sorghum halepense*), quackgrass (*Agropyron repens*), downy brome (*Bromus tectorum*), bermudagrass (*Cynodon dactylon*), etc.; Commelinaceae weeds such as dayflower (*Commelina communis*), etc.; and Cyperaceae weeds such as rice flatsedge (*Cyperus iria*), purple nutsedge (*Cyperus rotundus*), etc. In addition, the present compounds give such no phytotoxicity as becoming a problem to main crops such as corn, wheat, barley, rice, soybean, cotton, beet, etc.

In flooding treatment in paddy fields, the present compounds exhibit a herbicidal activity against gramineous weeds such as barnyardgrass (*Echinochloa oryzicola*), etc.; broad-leaved weeds such as false pimpernel (*Lindernia procumbens*), indian toothcup (*Rotala indica*), waterwort (*Elatine triandra*), Ammannia multiflora, etc.; Cyperaceae weeds such as smallflower umbrellaplant (*Cyperus difformis*), bulrush (*Scirpus juncoides*), slender spikerush (*Eleocharis acicularis*), water nutgrass (*Cyperus serotinus*), etc.; monochoria (*Monochoria vaginalis*), arrowhead (*Sagittaria pygmaea*), etc.

When the present compound (I) is used as an active ingredient for herbicides, it is usually formulated before use into emulsifiable concentrates, wettable powders, suspension formulations, granules, water-dispersible granules, etc. by mixing with solid carriers, liquid carriers, surface active agents or other auxiliaries for formulation.

The content of the compound (I) as an active ingredient in these preparations is normally within a range of about 0.001 to 90% by weight, preferably of about 0.003 to 80% by weight.

Examples of the solid carriers are fine powders or granules of kaolin clay, attapulgite clay, bentonite, terra abla, pyrophyllite, talc, diatomaceous earth, calcite, walnut shell powders, urea, ammonium sulfate and synthetic hydrated silicon dioxide, etc.

Examples of the liquid carriers are aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (soybean oil, cotton seed oil), dimethyl sulfoxide, N,N-dimethylformamide, acetonitrilo water, etc.

Examples of the surface active agents used for emulsification, dispersion or spreading, etc. are anionic surface active agents such as salts of alkyl sulfates, alkylsulfonates, alkylarylsulfonates, dialkyl sulfosuccinates, salts of polyoxyethylene alkylaryl ether phosphoric acid esters, etc., and nonionic surface active agents such as polyoxyethylene alkyl ethers, polyoxyethylene alkylaryl ethers, polyoxyethylene polyoxypropylene block copolymers, sorbitan fatty acid ester, polyoxyethylene sorbitan fatty acid esters, etc.

Examples of other auxiliaries for formulation are liganosulfonates, aliginates, polyvinyl alchol, gum arabic, CMC (carboxymethyl cellulose), PAP (isopropyl acid phosphate), etc.

The present compound (I) is usually formulated and used in soil treatment, foliar treatment or flooding treatment before or after emergence of weeds. The soil treatment includes soil surface treatment, soil incorporation treatment, etc. The foliar treatment includes, in addition to treatment of plants from above, directed treatment in which treatment is limited to weeds only so as not to adhere to crops.

Build-up of the herbicidal activity of the present compound (I) can be expected by using them in mixture with other herbicides. Further, the present compound (I) can also be used in mixture with insecticides, acaricides, nematocides, fungicides, plant growth regulators, fertilizes, soil improvers, etc.

The present compound (I) can be used as an active ingredient for herbicides used in paddy fields, ridges of paddy fields, plowed fields, non-plowed fields, orchards, pastures, turfs, forests and non-agricultural fields, etc.

When the present compound (I) is used as an active ingredient for herbicides, their dosage rate varies with weather conditions, preparation forms, when, how and where the treatment is carried out, weeds species to be controlled, crops species to be protected, etc. Usually, however, the dosage rate is from 0.003 grams to 100 grams of the active ingredient per are, preferably from 0.01 grams to 50 grams of the active gredient per are.

The herbicidal composition of the invention formulated in the form of an emulsifiable concentrate, a wettable powder or a suspension formulations may ordinarily be employed by diluting it with water at a volume of about 1 to 10 liters per are (if necessary, auxiliaries such as a spreading agent are added to the water). The granules are usually applied as they are without being diluted.

The spreading agent includes, in addition to the foregoing surface active agents, substances such as polyoxyethylene resin acids (esters), lignosulfonates, abietates, dinaphthylmethanedisulfonates, paraffin, etc.

The present invention will be illustrated in more detail with reference to the following production examples, formulation examples and test examples, which are not however to be interpreted as limiting the invention thereto.

First, production examples for the present compound (I) are shown.

PRODUCTION EXAMPLE 1

0.55 Gram of 2-(4,6-dimethoxypyrimidin-2-yl)oxybenzoic acid was dissolved in 3 ml of dry tetrahydrofuran, and 0.35 g of N,N'-carbonyldiimidazole was added. After stirring at room temperature for 20 minutes, a methylene chloride solution of N,N-dimethylhydroxylamine prepared from 0.39 g of N,N-dimethylhydroxylamine hydrochloride and 0.44 g of triethylamine was added, and stirring was carried out at room temperature for 12 hours. The reaction mixture was poured into a 1N hydrochloric acid, and the resulting mixed solution was extracted with ethyl acetate. The organic layer was separated, washed twice with a saturated aqueous sodium chloride solution and dried over anhydrous magnesium sulfate. The solvent was removed under reduced pressure, and the residue obtained was subjected to column chromatography on silica gel to obtain 0.50 g of 4,6-dimethoxy-2-{2-(N,N-dimethylaminooxycarbonyl)phenoxy]pyrimidine [present compound (1)].

Melting point: 71.0°–72.5° C.

$^1$H-NMR (CDCl$_3$) δ: 2.62 (s, 6H) 3.75 (s, 6H) 5.70 (s, 1H), 6.09–8.01 (m, 4H)

IR (nujol): 1750, 1614 cm$^{-1}$.

PRODUCTION EXAMPLE 2

0.55 Gram of 2-(4,6-dimethoxypyrimidin-2-yl)oxybenzoic acid was dissolved in 5 ml of dry tetrahydrofuran, and 0.35 g of N,N'-carbonyldiimidazole was added. After stirring at room temperature for 20 minutes, 0.20 g of N-hydroxypiperidine was added, and stirring was carried out at room temperature for 12 hours. The reaction mixture was poured into a 1N hydrochloric acid, and the resulting mixed solution was extracted with ethyl acetate. The organic layer was separated, washed twice with a saturated aqueous sodium chloride solution and dried over anhydrous magnesium sulfate. The solvent was removed under reduced pressure, and the residue obtained was subjected to column chromatography on silica gel to obtain 0.54 g of 20 4,6-dimethoxy-2-{2-(1-piperidyloxycarbonyl)phenoxy}-pyrimidine [present compound (2)].

$n_D^{22.7}$ 1.5454.

$^1$H-NMR (CDCl$_3$) δ: 1.0–3.5 (m, 10H), 3.74 (s, 6H) 5.69 (s, 1H), 7.07–8.00 (m, 4H). IR (neat): 2952, 1748, 1604 cm$^{-1}$.

PRODUCTION EXAMPLE 3

0.55 Gram of 2-(4,6-dimethoxypyrimidin-2-yl)oxybenzoic acid was dissolved in 3 ml of dry tetrahydrofuran. To the resulting solution was added a methylene chloride solution of N-tert-butylhydroxylamine prepared from 0.50 g of N-tert-butylhydroxylamine hydrochloride and 0.44 g of triethylamine. Subsequently, 0.85 g of 2,4,6-triisopropylbenzenesulfonyl chloride and 0.45 g of 1-methylimidazole were added, and the resulting mixture was stirred at room temperature for 3 hours. The reaction mixture was poured into a 1N hydrochloric acid, and the resulting mixed solution was extracted with ethyl acetate. The organic layer was separated, washed twice with a saturated aqueous sodium chloride solution and dried over anhydrous magnesium sulfate. The solvent was removed under reduced pressure, and the residue obtained was subjected to column chromatography on silica gel to obtain 0.30 g of 2-(2-(N-tert-butylaminooxycarbonyl)phenoxy]-4,6-dimethoxypyrimidine [present compound (3)].

$n_D^{25}$ 1.5351.

$^1$H-NMR (CDCl$_3$) δ: 1.10(s, 9H) 3.73(s, 6H), 5.69 (s, 1H), 6.45(bs, 1H), 7.10–8.04 (m, 4H).

IR (neat): 3240, 2980, 1716, 1602 cm$^{-1}$.

PRODUCTION EXAMPLE 4

0.17 Gram of a 60% sodium hydride in oil was suspended in 4 ml of N,N-dimethylformamide, and a solution of 0.70 g of 3- hydroxy-2-(N,N-dimethylaminooxycarbonyl)pyridine in 1 ml of N,N-dimethylformamide was added. After stirring at room temperature for 30 minutes, a solution of 0.84 g of 4,6-dimethoxy-2-methylsulfonylpyrimidine in 1 ml of N,N-dimethylformamide: was added. After stirring at room temperature for 3 hours, the reaction solution was heated to 70° to 80° C. and kept at the same temperature for 2 hours with stirring. The reaction solution was allowed to cool, poured into water and extracted with ethyl acetate. The organic layer was washed with water and dried over anhydrous magnesium sulfate. The solvent was removed under reduced pressure, and the residue obtained was subjected to chromatography to obtain 0.30 g of 3-(4,6-dimethoxypyrimidin-2-yl)oxy-2-(N,N-dimethylaminooxycarbonyl)pyridine [present compound (4)].

$^1$H-NMH (CDCl$_3$) δ: 2.72 (s, 6H), 3.78 (s, 6H), 5.76 (s, 1H), 7.55–7.63 (m, 2H), 8.61 (dxd, 1H, J=4.8, 2.4Hz).

PRODUCTION EXAMPLE 5

0.93 Gram of 2-chloro-6-(4,6-dimethoxypyrimidin-2-yl)oxybenzoic acid was dissolved in 10 ml of tetrahydrofuran, and 0.58 g of N,N'-carbonyldiimidazole was added. After stirring at room temperature for 10 minutes, the solution was refluxed for 20 minutes. After the solution was allowed to cool, 0.35 g of N,N-dimethylhydroxylamine hydrochloride and 0.36 g of triethylamine were added, and the resulting mixed solution was stirred overnight at room temperature. The reaction solution was poured into water and extracted with ethyl acetate. The organic layer was separated, washed twice with a saturated aqueous sodium chloride solution and dried over anhydrous magnesium sulfate. The solvent was removed under reduced pressure, and the residue obtained was subjected to chromatography on silica gel to obtain 0.2 g of 4,6-dimethoxy-2-(3-chloro-2-(N,N-dimethylaminooxycarbonyl)phenoxy}pyrimidine [present compound (12)].

m.p. 80.0°–81.0° C.

$^1$H-NMR (CDCl$_3$) δ: 2.73 (s, 6H), 3.77 (s, 6H), 5.72 (s, 1H), 7.00–7.49 (m, 3H).

PRODUCTION EXAMPLE 6

1.98 Grams of 2-fluoro-6-(4,6-dimethoxypyrimidin-2-yl)oxybenzoic acid was dissolved in 20 ml of tetrahydrofuran, and 1.31 g of N,N-carbonyldiimidazole was added. After stirring at room temperature for 20 minutes, 0.80 g of N,N-dimethylhydroxylamine hydrochloride and 0.83 g of triethylamine were added, and the resulting mixed solution was stirred at room temperature for 6 hours. The reaction solution was poured into water and extracted with ethyl acetate. The organic layer was separated, washed twice with a saturated aqueous sodium chloride solution and dried over anhydrous magnesium sulfate. The solvent was removed under reduced pressure, and the residue obtained was subjected to chromatography on silica gel to obtain 1.10 g of 4,6-dimethoxy-2-{3-fluoro-2-(N,N-dimethylaminooxycarbonyl)phenoxy}pyrimidine [present compound (13)].

$^1$H-NMR (CDCl$_3$) δ: 2.68 (s, 6H), 3.77 (s, 6H), 5.72 (s, 1H), 6.82–7.62 (m, 3H).

The present compounds thus obtained are collectively shown in Table 3

TABLE 3

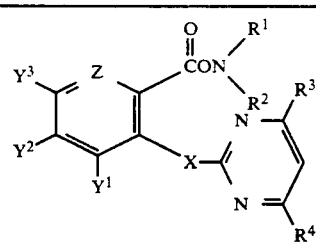

| Compound No. | R$^1$ | R$^2$ | Y$^1$ | Y$^2$ | Y$^3$ | X | Z | R$^3$ | R$^4$ | Physical properties (m.p., refractive index, $^1$H-NMR (CDCl$_3$, δ) |
|---|---|---|---|---|---|---|---|---|---|---|
| (1) | CH$_3$ | CH$_3$ | H | H | H | O | CH | OCH$_3$ | OCH$_3$ | m.p. 71.0° C.~72.5° C. |
| (2) | ⁺CH$_2$⁾$_5$ | | H | H | H | O | CH | OCH$_3$ | OCH$_3$ | $n_D^{22.7}$ 1.5454 |
| (3) | H | tert-C$_4$H$_9$ | H | H | H | O | CH | OCH$_3$ | OCH$_3$ | $n_D^{25}$ 1.5351 |
| (4) | CH$_3$ | CH$_3$ | H | H | H | O | N | OCH$_3$ | OCH$_3$ | $n_D^{25}$ 1.5440 |
| (5) | CH$_3$ | CH$_3$ | H | CH$_3$ | H | O | CH | OCH$_3$ | OCH$_3$ | $n_D^{24}$ 1.5375 |
| (6) | CH$_3$ | CH$_3$ | H | Cl | H | O | CH | OCH$_3$ | OCH$_3$ | $n_D^{24}$ 1.5418 |
| (7) | CH$_3$ | CH$_3$ | H | H | H | O | CH | CH$_3$ | CH$_3$ | 2.32(S, 6H), 2.55(S, 6H), 6.65(S, 1H), 7.08–8.00(m, 4H) |
| (8) | CH$_3$ | CH$_3$ | H | H | H | O | CH | OCH$_3$ | Cl | $n_D^{25}$ 1.5420 |
| (9) | CH$_3$ | CH$_3$ | H | H | Cl | O | CH | OCH$_3$ | OCH$_3$ | $n_D^{22}$ 1.5415 |
| (10) | CH$_3$ | CH$_3$ | H | H | F | O | CH | OCH$_3$ | OCH$_3$ | $n_D^{22}$ 1.5231 |
| (11) | CH$_3$ | CH$_3$ | H | H | OCH$_3$ | O | CH | OCH$_3$ | OCH$_3$ | $n_D^{22}$ 1.5342 |

TABLE 3-continued

Structure:

$$\begin{array}{c}\text{Y}^3\!-\!\text{Z}\!-\!\text{C(=O)N(R}^1)(\text{R}^2)\text{-aryl-X-pyrimidine(R}^3,\text{R}^4)\end{array}$$

| Compound No. | R¹ | R² | Y¹ | Y² | Y³ | X | Z | R³ | R⁴ | Physical properties (m.p., refractive index, ¹H-NMR (CDCl₃, δ) |
|---|---|---|---|---|---|---|---|---|---|---|
| (12) | CH₃ | CH₃ | H | H | H | O | CCl | OCH₃ | OCH₃ | m.p. 80.0–81.0° C. |
| (13) | CH₃ | CH₃ | H | H | H | O | CF | OCH₃ | OCH₃ | $n_D^{23}$ 1.5271 |
| (14) | CH₃ | CH₃ | H | H | H | O | CF | OCH₃ | Cl | m.p. 100.0–102.0° C. |
| (15) | CH₃ | CH₃ | H | H | H | S | CH | OCH₃ | OCH₃ | $n_D^{24}$ 1.5672 |
| (16) | CH₃ | CH₃ | Cl | H | H | O | CH | OCH₃ | OCH₃ | $n_D^{24}$ 1.5378 |
| (17) | CH₃ | CH₃ | CH₃ | H | H | O | CH | OCH₃ | OCH₃ | $n_D^{24}$ 1.5403 |
| (18) | CH₃ | CH₃ | H | H | CH₃ | O | CH | OCH₃ | OCH₃ | $n_D^{24}$ 1.5315 |
| (19) | CH₃ | CH₃ | H | OCH₃ | H | O | CH | OCH₃ | OCH₃ | $n_D^{24}$ 1.5513 |
| (20) | H | tert-C₄H₉ | H | H | H | O | CF | OCH₃ | OCH₃ | m.p. 89.0–90.0° C. |
| (21) | ⟨CH₂⟩₅ | H | H | H | H | O | CF | OCH₃ | OCH₃ | $n_D^{24}$ 1.5351 |
| (22) | CH₃ | CH₃ | OCH₃ | H | H | O | CH | OCH₃ | OCH₃ | $n_D^{24}$ 1.5361 |
| (23) | CH₃ | CH₃ | H | H | H | O | CCF₃ | OCH₃ | OCH₃ | $n_D^{24}$ 1.5045 |
| (24) | CH₂C₆H₅ | CH₂C₆H₅ | H | H | H | O | CF | OCH₃ | OCH₃ | $n_D^{25}$ 1.5538 |
| (25) | CH₂C₆H₅ | CH₂C₆H₅ | H | H | H | O | CH | OCH₃ | OCH₃ | m.p. 114.0–115.0° C. |
| (26) | CH₂C₆H₅ | CH₂C₆H₅ | H | H | H | O | N | OCH₃ | OCH₃ | $n_D^{25}$ 1.5678 |
| (27) | H | C₃H₇(i) | H | H | H | O | CH | OCH₃ | OCH₃ | $n_D^{25}$ 1.5454 |
| (28) | H | CH₃ | H | H | H | O | CH | OCH₃ | OCH₃ | $n_D^{25}$ 1.5462 |
| (29) | H | C₃H₇(i) | H | H | H | O | N | OCH₃ | OCH₃ | $n_D^{25}$ 1.5326 |
| (30) | ⟨CH₂⟩₅ | | H | H | H | O | CCl | OCH₃ | OCH₃ | $n_D^{25}$ 1.5328 |
| (31) | H | tert-C₄H₉ | H | H | H | O | CCl | OCH₃ | OCH₃ | $n_D^{24}$ 1.5375 |
| (32) | ⟨CH₂⟩₅ | | H | H | H | O | CCF₃ | OCH₃ | OCH₃ | $n_D^{24}$ 1.5411 |
| (33) | CH₃ | CH₃ | H | H | H | O | CCH₃ | OCH₃ | OCH₃ | $n_D^{23}$ 1.5378 |
| (34) | H | cyclohexyl | H | H | H | O | CH | OCH₃ | OCH₃ | $n_D^{24}$ 1.5321 |
| (35) | H | cyclohexyl | H | H | H | O | N | OCH₃ | OCH₃ | $n_D^{24}$ 1.5337 |
| (36) | —CH₂CH₂—O—CH₂CH₂— | | H | H | H | O | CCl | OCH₃ | OCH₃ | $n_D^{26.5}$ 1.5523 |
| (37) | —CH₂CH₂—O—CH₂CH₂— | | H | H | H | O | N | OCH₃ | OCH₃ | $n_D^{24}$ 1.5430 |
| (38) | H | CH₃ | H | H | H | O | CCl | OCH₃ | OCH₃ | $n_D^{24}$ 1.5623 |
| (39) | H | C₃H₇(i) | H | H | H | O | CCl | OCH₃ | OCH₃ | 1.09(d, 6H, J=6.0Hz), 3.35 (sep, 1H, J=6.0Hz), 3.77(s, 6H), 5.72(s, 1H), 6.82–7.35 (m, 3H) |
| (40) | H | cyclohexyl | H | H | H | O | CCl | OCH₃ | OCH₃ | $n_D^{24}$ 1.5458 |
| (41) | CH₂C₆H₅ | CH₂C₆H₅ | H | H | H | O | CCl | OCH₃ | OCH₃ | m.p. 57.0–59.0° C. |
| (42) | ⟨CH₂⟩₅ | | H | H | H | O | N | OCH₃ | OCH₃ | $n_D^{24}$ 1.5352 |
| (43) | CH₃ | CH₃ | H | H | H | O | COCH₃ | OCH₃ | OCH₃ | m.p 115–117° C. |
| (44) | CH₃ | CH₃ | H | H | H | O | CC₆H₅ | OCH₃ | OCH₃ | 2.37(s, 6H), 3.79(s, 6H), 5.70 (s1H 7.07–7.57(m, 8H) |
| (45) | CH₃ | CH₃ | H | H | H | O | CCOOCH₂ | OCH₃ | OCH₃ | 2.86(s, 6H), 3.78(s, 6H), 5.73(s, 1H) 7.30–7.91(m, 3H) |
| (46) | CH₃ | CH₃ | H | H | H | O | CNO₂ | OCH₃ | OCH₃ | 2.76(s, 6H), 3.76(s, 6H), 5.52(s, 1H) 7.17(t, 1H, J=3.8Hz), 7.92–8.19(m, 2H) |
| (47) | CH₂CH₂OCH₃ | CH₂CH₂OCH₃ | H | H | H | O | CCl | OCH₃ | OCH₃ | $n_D^{23.5}$ 1.5385 |
| (48) | —CH(CH₃)CH₂CH₂CH₂CH(CH₃)— | | H | H | H | O | CCl | OCH₃ | OCH₃ | $n_D^{23.5}$ 1.5374 |
| (49) | CH₃ | CH₂C₆H₅ | H | H | H | O | CCl | OCH₃ | OCH₃ | $n_D^{23.5}$ 1.5635 |
| (50) | CH₂CH₂Cl | CH₂CH₂Cl | H | H | H | O | CH | OCH₃ | OCH₃ | $n_D^{23.5}$ 1.5386 |

TABLE 3-continued

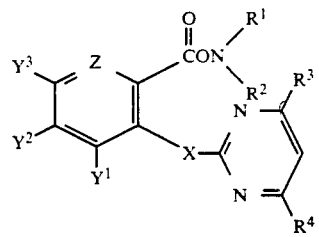

| Compound No | R¹ | R² | Y¹ | Y² | Y³ | X | Z | R³ | R⁴ | Physical properties (m.p., refractive index, ¹H-NMR (CDCl₃, δ) |
|---|---|---|---|---|---|---|---|---|---|---|
| (51) | CH₃ | C₂H₅ | H | H | H | O | CCl | OCH₃ | OCH₃ | $n_D^{23.5}$ 1.5270 |
| (52) | CH₂CH₂CN | CH₂CH₂CN | H | H | H | O | CCl | OCH₃ | OCH₃ | 2.63(t, 4H, J=5.0Hz), 2.93(t, 4H J=5.0Hz), 3.78(s, 6H), 5.71 (s, 1H), 7.01-7.46(m, 3H) |
| (53) | (CH₂)₄ | | H | H | H | O | CCl | OCH₃ | OCH₃ | $n_D^{23.5}$ 1.5468 |
| (54) | CH₂COOC₂H₅ | CH₂COOC₂H₅ | H | H | H | O | CCl | OCH₃ | OCH₃ | $n_D^{25}$ 1.5332 |

1 Production examples for the phenol derivatives (II), a starting compound, are shown.

PRODUCTION EXAMPLE 7

6.00 Grams of acetylsalicylic acid chloride was dissolved in 70 ml of methylene chloride, and 7.37 g of N,N-dimethylhydroxylamine hydrochloride was added. Then, 9.16 of triethylamine was added dropwise thereto with stirring at room temperature. After completion of addition, stirring was carried out at room temperature for further 6 hours. The reaction mixture was washed with a 0.5N hydrochloric acid and then twice with water, and dried over anhydrous magnesium sulfate. The solvent was removed under reduced pressure, and the residue obtained was subjected to column chromatography to obtain 3.10 g of 2-(N,N-dimethylaminooxycarbonyl)phenol.

¹H-NMR (CDCl₃) δ: 2.90 (s, 6H), 6.68-7.81 (m, 4H), 10.65 (bs, 1H).

PRODUCTION EXAMPLE 8

7.0 Grams of 3-hydroxypicolinic acid was dissolved in 10 ml of N,N-dimethylformamide, and the resulting solution was cooled to 0° to 5° C. 5.9 Grams of thionyl chloride was then added dropwise to the solution which was then stirred at 0° to 5° C. for further 30 minutes. Thereafter, 30 ml of chloroform was added to the solution which was then stirred at 0° to 5° C. for further 15 minutes. To the resulting mixed solution was added dropwise a dichloromethane solution of N,N-dimethylhydroxylamine prepared from 7.4 g of N,N-dimethylhydroxylamine hydrochloride and 7.6 g of triethylamine. After stirring at 0° to 5° C. for 30 minutes, 7.9 g of pyridine was added, and stirring was continued at 0° to 5° C. for further 1 hour. After stirring at room temperature for 8 hours, the reaction solution was poured into water, and insoluble matters were removed by filtration on celite. The organic layer was washed with water and dried over anhydrous magnesium sulfate. The solvent was removed under reduced pressure, and the residue obtained was subjected to chromatography to obtain 1.0 g of 3-hydroxy-2-(N,N-dimethylaminooxycarbonyl)-pyridine.

¹H-NMR (CDCl₃) δ: 2.97 (s, 6H), 7.31-7.36 (m, 2H), 8.20 (dxd, 1H, J=3.0, 4.0Hz), 10.30 (bs, 1H).

PRODUCTION EXAMPLE 9

1.56 Grams of 6-fluorosalicylic acid was dissolved in 20 ml of tetrahydrofuran, and 1.94 g of N,N'-carbonyldiimidazole was added. After stirring at room temperature for 30 minutes, 1.47 g of N,N-dimethylhydroxylamine hydrochloride and 1.52 g of triethylamine were added, and the resulting mixed solution was stirred at room temperature for 7 hours. The reaction solution was poured into water and extracted with ethyl acetate. The organic layer was washed with a saturated aqueous sodium chloride solution and dried over anhydrous magnesium sulfate. The solvent was removed under reduced pressure, and the residue obtained was subjected to column chromatography to obtain 0.6 g of 3-fluoro-2-(N,N-dimethylaminooxycarbonyl)phenol.

¹H-NMR (CDCl₃) δ: 2.91 (s, 6H), 6.36-7.50 (m, 4H), 11.05 (s, 1H).

PRODUCTION EXAMPLE 10

1.73 Grams of 6-chlorosalicylic acid was dissolved in 20 ml of tetrahydrofuran, and 1.95 g of N,N'-carbonyldiimidazole was added. After stirring at room temperature for 30 minutes, 1.47 g of N,N-dimethylhydroxylamine hydrochloride and 1.52 g of triethylamine were added, and the resulting mixed solution was stirred at room temperature for 7 hours. The reaction solution was poured into water and extracted with ethyl acetate. The organic layer was washed with a saturated aqueous sodium chloride solution and dried over anhydrous magnesium sulfate. The solvent was removed under reduced pressure, and the residue obtained was subjected to column chromatography to obtain 1.1 g of 3-chloro-2-(N,N-dimethylaminooxycarbonyl)phenol.

¹H-NMR (CDCl₃) δ: 2.92 (s, 6H), 6.74-7.35 (m, 6H), 10.30 (s, 1H).

m.p. : 104°-106° C.

The phenol derivatives (II) thus obtained are collectively shown in Table 4.

TABLE 4

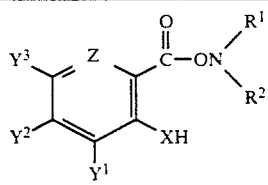

| R¹ | R² | Y¹ | Y² | Y³ | Z | X | Physical properties (m.p., refractive index, ¹H-NMR (CDCl₃, δ)) |
|---|---|---|---|---|---|---|---|
| CH₃ | CH₃ | H | H | H | CH | O | 2.90(s, 6H), 6.68-7.81(m, 4H), 10.65(bs, 1H) |
| CH₃ | CH₃ | H | H | H | N | O | 2.97(s, 6H), 7.31-7.36(m, 2H), 8.20(dxd, 1H, J=3.0, 4.0Hz), 10.30 (bs, 1H) |
| CH₃ | CH₃ | H | H | H | CF | O | 2.91(s, 6H), 6.36-7.50(m, 4H), 11.05(s, 1H) |
| CH₃ | CH₃ | H | H | H | CCl | O | m.p. 104-106° C. |
| CH₃ | CH₃ | CH₃ | H | H | CH | O | $n_D^{24}$ 1.5272 |
| CH₂C₆H₅ | CH₂C₆H₅ | H | H | H | CH | S | $n_D^{24}$ 1.6118 |
| H | C₄H₉(tert) | H | H | H | CH | O | $n_D^{24}$ 1.5148 |
| H | C₄H₉(tert) | H | H | H | CCl | O | $n_D^{24}$ 1.5019 |
| CH₂C₆H₅ | CH₂C₆H₅ | H | H | H | CH | O | m.p 94-95° C. |
| CH₂C₆H₅ | CH₂C₆H₅ | H | H | H | CCl | O | m.p 116-117° C. |
| ⁺CH₂₇ | | H | H | H | CH | O | $n_D^{24}$ 1.5383 |
| ⁺CH₂₇ | | H | H | H | CCl | O | m.p 136-137° C. |

Formulation examples are shown below. In the examples, the present compound (I) is shown by Compound No. in Table 3, and parts are by weight.

FORMULATION EXAMPLE 1

Fifty parts of the present compound (1), (12), (14), (20), (25), 3 parts of calcium lignosulfonate, 2 parts of sodium lauryl sulfate and 45 parts of synthetic hydrated silicon dioxide are well mixed while being powdered to obtain a wettable powder.

FORMULATION EXAMPLE 2

Ten parts of the present compound (1)-(32), 14 parts of polyoxyethylene styrylphenyl ether, 6 parts of calcium dodecylbenzenesulfonate, 40 parts of xylene and 30 parts of cyclohexanone are well mixed to obtain an emulsifiable concentrate.

FORMULATION EXAMPLE 3

Two parts of the present compound (1), (12), (14), (20), (25), 1 part of synthetic hydrated silicon dioxide, 2 parts of calcium lignosulfonate, 30 parts of bentonite and 65 parts of kaolin clay are well pulverized and mixed. The resulting mixture is well kneaded with water, granulated and dried to obtain a granule.

FORMULATION EXAMPLE 4

Twenty five parts of the present compound (1)-(32), 3 parts of polyoxyethylene sorbitan monooleate, 3 parts of CMC and 69 parts of water are mixed and wet-pulverized until the particle size decreases to 5 microns or less. Thus, a suspension formulation is obtained.

That the present compounds are useful as an active ingredient for herbicides is shown by test examples. In the examples, the present compound (I) is shown by Compound No. in Table 3, and compounds used for comparison are shown by Compound symbol in Table 5.

TABLE 5

| Compound symbol | Structural formula | Remarks |
|---|---|---|
| A | (structure with COOC₂H₅, OCH₃, CH₃ substituents) | Japanese Patent Application Kokai No. 63-115870. ($n_D^{23}$ 1.5271) |
| B | (structure with CON(CH₃)₂, OCH₃) | Comparative compound ($n_D^{23}$ 1.5475) |
| C | (structure with COOH, OCH₃, CH₃) | Japanese Patent Application Kokai No. 63-115870. |
| D | (structure with COOCH₃, CH₃, OCH₃) | Japanese Patent Application Kokai No. 62-174059. |
| E | (structure with COOC₂H₅, OCH₃) | Japanese Patent Application Kokai No. 62-174059. |
| F | (structure with COON=C(CH₃)₂, OCH₃) | Japanese Patent Application Kokai No. 62-174059. |

TABLE 5-continued

| Compound symbol | Structural formula | Remarks |
|---|---|---|
| G | (structure: benzene with CO-(CH₂)₂-N(CH₃)₂ and O-C(=N-)(N=) pyrimidine with two OCH₃ groups) | Comparative compound ($n_D^{19}$ 1.5298) |
| H | (structure: benzene with COO⁻H₃N⁺-CH(CH₃)(OCH₃)(CH₃) and O-pyrimidine with two OCH₃) | Japanese Patent Application Kokai No. 62-174059. |
| I | (structure: benzene with C(=O)-O-CH(CH₃)₂ and O-pyrimidine with two OCH₃) | Japanese Patent Application Kokai No. 62-174059. |
| J | (structure: pyridine with C(=O)-O-CH(CH₃)₂ and O-pyrimidine with two OCH₃) | Japanese Patent Application Kokai No. 64-84. |
| K | (structure: pyridine with COCH₃ and O-pyrimidine with two OCH₃) | Japanese Patent Application Kokai No. 64-84. |
| L | (structure: pyridine with COH and O-pyrimidine with two OCH₃) | Japanese Patent Application Kokai No. 64-84. |
| M | (structure: pyridine with C(=O)-O-N=C(CH₃)₂ and O-pyrimidine with two OMe) | Japanese Patent Application Kokai No. 1-250378. |

The evaluation of the herbicidal activity and phytotoxicity was carried out as follows: When the states of emergence and growth of treated test plants (weeds and crops) at the time of evaluation were completely the same as or hardly different from those of untreated test plants, the value of evaluation was taken as "0". When the treated test plants were completely killed, or their emergence and growth were completely inhibited, the value of evaluation was taken as "5", and an interval between "0" and "5" was divided into four stages, i.e. "1", "2", "3" and "4". The evaluation was thus made in six stages.

TEST EXAMPLE 1

Soil surface treatment test in upland field soil

Cylindrical plastic pots of 10 cm in diameter and 10 cm in depth were filled with upland field soil, and the seeds of Japanese millet, oat, tall morningglory and velvetleaf were sowed in the respective pots and covered with soil. The test compounds were formulated into emulsifiable concentrates according to Formulation example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in Table 6.

TABLE 6

| Test compound | Dosage rate of active ingredient (g/a) | Japanese millet | Oat | Tall morningglory | Velvetleaf |
|---|---|---|---|---|---|
| (1) | 5 | 5 | 5 | — | 5 |
|  | 1.25 | 5 | 4 | — | 4 |
| (2) | 5 | 5 | 5 | 4 | 4 |
|  | 1.25 | 5 | 4 | — | 4 |
| (3) | 5 | 5 | 5 | — | 5 |
|  | 1.25 | 5 | 4 | — | 4 |
| (8) | 5 | 4 | 4 | — | — |
| (10) | 5 | 5 | 4 | — | 4 |
|  | 1.25 | 4 | 4 | — | 4 |
| (11) | 5 | 5 | 4 | — | — |
| (12) | 5 | 5 | 5 | 5 | 5 |
|  | 1.25 | 5 | 5 | 4 | 5 |
|  | 0.31 | 5 | 4 | 4 | 5 |
| (13) | 5 | 5 | 5 | 5 | 5 |
|  | 1.25 | 5 | 5 | 4 | 5 |
|  | 0.31 | 5 | 5 | 4 | 5 |
| (14) | 5 | 5 | 4 | — | 4 |
|  | 1.25 | 4 | 4 | — | 4 |
| (20) | 5 | 5 | 5 | 4 | 5 |
|  | 1.25 | 5 | 5 | 4 | 5 |
|  | 0.31 | 5 | 5 | — | 4 |

TABLE 6-continued

| Test compound | Dosage rate of active ingredient (g/a) | Herbicidal activity | | | |
|---|---|---|---|---|---|
| | | Japanese millet | Oat | Tall morning-glory | Velvet-leaf |
| (21) | 5 | 5 | 5 | 4 | 5 |
| | 1.25 | 5 | 5 | 4 | 4 |
| | 0.31 | 5 | 4 | — | 4 |
| (23) | 5 | 5 | 4 | 4 | 4 |
| | 1.25 | 5 | — | 4 | 4 |
| (24) | 5 | 5 | 4 | — | 4 |
| | 1.25 | 5 | 4 | — | 4 |
| (25) | 5 | 5 | 4 | — | 4 |
| (27) | 5 | 5 | 5 | 4 | 4 |
| | 1.25 | 5 | 4 | — | 4 |
| (28) | 5 | 5 | 4 | — | 4 |
| (29) | 5 | 5 | 4 | — | 4 |
| (30) | 5 | 5 | 4 | 4 | 4 |
| | 1.25 | 5 | 4 | 4 | 4 |
| (31) | 5 | 5 | 4 | 4 | 5 |
| | 1.25 | 5 | 4 | 4 | 5 |
| (32) | 5 | 5 | 4 | 4 | 5 |
| | 1.25 | 5 | — | 4 | 4 |
| A | 5 | 4 | 3 | 0 | 1 |
| | 1.25 | 2 | 1 | — | 0 |
| B | 5 | 0 | 0 | 0 | 0 |
| | 1.25 | 0 | 0 | — | 0 |
| C | 5 | 4 | 3 | 0 | 2 |
| | 1.25 | 2 | 1 | — | 0 |
| D | 5 | 3 | 3 | 0 | 1 |
| | 1.25 | 1 | 2 | — | 0 |
| G | 5 | — | 3 | 0 | — |
| | 1.25 | 2 | 2 | 0 | 2 |
| L | 5 | 2 | 2 | 0 | 3 |
| | 1.25 | 1 | 0 | 0 | 2 |
| M | 5 | 3 | 2 | 0 | 3 |
| | 1.25 | 0 | 0 | 0 | 2 |

TEST EXAMPLE 2

Foliar treatment test in upland field soil

Cylindrical plastic pots of 10 cm in diameter and 10 cm in depth were filled with upland field soil, and the seeds of Japanese millet, oat, radish and velvetleaf were sowed in the respective pots and cultivated for 8 days in a greenhouse.

Thereafter, the test compounds were formulated into emulsifiable concentrates according to Formulation example 2, and the prescribed amount of each emulsifiable concentrate was diluted with a spreading agent-containing water corresponding to 10 liters/are and uniformly applied from above onto the whole foliar portion of the test plants by means of an automatic sprayer. After application, the test plants were cultivated for 19 days in a greenhouse, and the herbicidal activity was examined.

The results are shown in Table 7.

TABLE 7

| Test compound | Dosage rate of active ingredient (g/a) | Herbicidal activity | | | |
|---|---|---|---|---|---|
| | | Japanese millet | Oat | Radish | Velvet-leaf |
| (1) | 5 | 5 | 5 | 4 | 5 |
| (2) | 5 | 5 | 5 | — | 4 |
| (3) | 5 | 5 | 5 | 4 | 5 |
| (4) | 5 | 5 | 5 | 5 | 5 |
| | 1.25 | 5 | 5 | 5 | 5 |
| (10) | 5 | 4 | — | 5 | 5 |
| (11) | 5 | 5 | — | 5 | — |
| (12) | 5 | 5 | 5 | 5 | 5 |
| | 1.25 | 5 | 5 | 5 | 5 |
| (13) | 5 | 5 | 5 | 5 | 5 |
| | 1.25 | 5 | 5 | 5 | 5 |
| (20) | 5 | 5 | 5 | 5 | 5 |

TABLE 7-continued

| Test compound | Dosage rate of active ingredient (g/a) | Herbicidal activity | | | |
|---|---|---|---|---|---|
| | | Japanese millet | Oat | Radish | Velvet-leaf |
| | 1.25 | 4 | 5 | 5 | 5 |
| (21) | 5 | 5 | 5 | 5 | 5 |
| | 1.25 | 4 | 5 | 5 | 5 |
| (23) | 5 | 5 | 4 | 5 | 5 |
| | 1.25 | 5 | — | 5 | 5 |
| (24) | 5 | 5 | 5 | 5 | 5 |
| | 1.25 | 4 | 4 | 5 | 5 |
| (25) | 5 | 4 | 4 | 4 | — |
| (26) | 5 | 5 | 5 | 5 | 5 |
| | 1.25 | 4 | 4 | 4 | 4 |
| (27) | 5 | 5 | 5 | 4 | 4 |
| | 1.25 | 4 | 4 | 4 | — |
| (28) | 5 | 5 | 4 | 5 | 4 |
| | 1.25 | 4 | 4 | 4 | — |
| (29) | 5 | 5 | 5 | 5 | 5 |
| | 1.25 | 5 | 5 | 5 | 5 |
| (30) | 5 | 5 | 5 | 5 | 5 |
| | 1.25 | 5 | 4 | 5 | 5 |
| (31) | 5 | 5 | 5 | 5 | 5 |
| | 1.25 | 5 | 4 | 5 | 5 |
| (32) | 5 | 5 | — | 5 | 5 |
| | 1.25 | 5 | — | 5 | 5 |
| A | 5 | 4 | 2 | 1 | 1 |
| B | 5 | 0 | 0 | 0 | 0 |
| C | 5 | 3 | 3 | 1 | 12 |
| D | 5 | 3 | 2 | 2 | 1 |
| I | 5 | 2 | 2 | 2 | 2 |
| J | 5 | 4 | — | 2 | — |
| | 1.25 | 2 | 2 | 1 | — |

TEST EXAMPLE 3

Soil treatment test in upland field soil

Vats of 33×23 cm2 in area and 11 cm in depth were filled with upland field soil, and the seeds of barnyardgrass, johnsongrass, green foxtail, wild oat and blackgrass were sowed in the respective vats and covered with soil in a thickness of 1 to 2 cm. The test compounds were formulated into emulsifiable concentrates according to Formulation example 2, and the prescribed amount of each emulsifiable concentrate was diluted with water corresponding to 10 liters/are and uniformly applied onto the whole soil surface by means of an automatic sprayer. After application, the test plants were cultivated for 18 days in a greenhouse, and the herbicidal activity was examined. The results are shown in Table 8.

TABLE 8

| Test compound | Dosage rate of active ingredient (g/a) | Herbicidal activity | | | | |
|---|---|---|---|---|---|---|
| | | Barn-yard-grass | Johnson-grass | Green foxtail | Wild oat | Black-grass |
| (1) | 10 | 5 | 5 | 5 | 4 | 5 |
| | 2.5 | 4 | 4 | 4 | 4 | 5 |
| (2) | 10 | 5 | 5 | 5 | 4 | — |
| | 2.5 | 4 | 4 | 5 | 4 | — |
| A | 10 | 3 | 4 | 2 | 3 | 3 |
| | 2.5 | 2 | 3 | 1 | 1 | 3 |

TEST EXAMPLE 4

Foliar treatment test in upland field soil

Vats of 33×33 cm² in area and 11 cm in depth were filled with upland field soil, and the seeds of cron, barnyardgrass and green foxtail were sowed in the respective vats and cultivated for 16 days. Thereafter, the test compounds were formulated into emulsifiable concentrates according to Formulation example 2, and the prescribed amount of each emulsifiable concentrate was diluted with water corresponding to 10 liters/are and uniformly applied from above onto the whole foliar portion of the test plants by means of an automatic sprayer. The condition of growth of the weeds and crop at that time varied with the kind of the test plants, but the test plants were in the 1- to 4-leaf stage and were 5 to 12 cm in height. Eighteen days after application, the herbicidal activity and phytotoxicity were examined.

respective vats and covered with soil in a thickness of 1 to 2 cm. The test compounds were formulated into emulsifiable concentrates according to Formulation example 2, and the prescribed amount of each emulsifiable concentrate was diluted with water corresponding to 10 liters/are and uniformly applied onto the whole soil surface by means of an automatic sprayer.

After application, the test plants were cultivated for 18 days in a greenhouse, and the herbicidal activity and phytotoxicity were examined. The results are shown in Table 10.

TABLE 10

| Test compound | Dosage rate of active ingredient (g/a) | Phytotoxicity | | | Herbicical activity | | | | |
|---|---|---|---|---|---|---|---|---|---|
| | | Soybean | Cotton | Corn | Black nightshade | Velvetleaf | Barnyardgrass | Green foxtail | Johnsongrass |
| (1) | 5 | — | — | — | 5 | 5 | 5 | 5 | 5 |
| | 1.25 | 0 | 0 | 0 | 5 | 4 | 4 | 4 | 4 |
| (2) | 5 | 1 | — | — | 5 | 5 | 5 | 5 | 4 |
| | 1.25 | 0 | 0 | — | 4 | 4 | 4 | 5 | 4 |
| (3) | 5 | — | — | — | 4 | — | 4 | 5 | 4 |
| | 1.25 | 0 | 0 | 0 | 4 | — | — | — | 4 |
| (5) | 5 | 0 | 0 | 0 | 4 | — | — | — | — |
| (10) | 1.25 | 1 | — | 0 | 4 | 4 | 4 | — | 4 |
| (11) | 5 | 1 | 0 | 0 | — | — | 4 | 4 | 4 |
| (23) | 1.25 | — | 1 | — | 5 | 4 | 5 | 4 | 5 |
| | 0.32 | — | 0 | 1 | 5 | 4 | 4 | 4 | 4 |
| A | 5 | 2 | 2 | 0 | 0 | 0 | 2 | 1 | 3 |
| | 1.25 | 0 | 2 | 0 | 0 | 0 | 1 | 0 | 2 |
| B | 5 | 0 | 0 | 0 | 0 | 0 | 0 | 0 | 0 |
| C | 5 | 0 | 0 | 0 | 0 | 0 | 3 | 3 | 3 |
| | 1.25 | 0 | 0 | 0 | 0 | 0 | 3 | 0 | 1 |
| D | 5 | 0 | 0 | 0 | 0 | 0 | 1 | 1 | 0 |
| L | 5 | 0 | 0 | 0 | 2 | 2 | 0 | 1 | 0 |
| | 1.25 | 0 | 0 | 0 | 1 | 1 | 0 | 0 | 0 |

The results are shown in Table 9. This test was carried out in a greenhouse through the whole test period.

TABLE 9

| Test compound | Dosage rate of active ingredient (g/a) | Phytotoxicity Corn | Herbicidal activity | |
|---|---|---|---|---|
| | | | Barnyardgrass | Green foxtail |
| (1) | 2.5 | 0 | 4 | 5 |
| | 0.63 | 0 | 4 | 4 |
| (2) | 2.5 | 2 | 4 | 5 |
| | 0.63 | 0 | 4 | 5 |
| A | 2.5 | 0 | 2 | 0 |
| | 0.63 | 0 | 1 | 0 |
| E | 2.5 | 4 | 4 | 0 |
| | 0.63 | 1 | 3 | 0 |

TEST EXAMPLE 5

Soil treatment test in upland field soil

Vats of 33×23 cm² in area and 11 cm in depth were filled with upland field soil, and the seeds of soybean, cotton, corn, velvetleaf, black nightshade, barnyardgrass, green foxtail and johnsongrass were sowed in the

TEST EXAMPLE 6

Foliar treatment test in upland field soil

Vats of 33×23 cm² in area and 11 cm in depth were filled with upland field soil, and the seeds of corn, tall morningglory, cocklebur, velvetleaf, sicklepod, black nightshade, barnyardgrass, green foxtail and johnsongrass were sowed in the respective vats and cultivated for 16 days. Thereafter, the test compounds were formulated into emulsifiable concentrates according to Formulation example 2, and the prescribed amount of each emulsifiable concentrate was diluted with water corresponding to 10 liters/are and uniformly applied from above onto the whole foliar portion of the test plants by means of an automatic sprayer. The condition of growth of the weeds and crop at that time varied with the kind of the test plants, but the test plants were in the 0.5- to 4-leaf stage and were 5 to 30 cm in height. Eighteen days after application, the herbicidal activity and phytotoxicity were examined. The results are shown in Table 11. This test was carried out in a greenhouse through the whole test period.

TABLE 11

| Test compound | Dosage rate of active ingredient (g/a) | Phytotoxicity Corn | Herbicidal activity | | | | | | | |
|---|---|---|---|---|---|---|---|---|---|---|
| | | | Tall morningglory | Cocklebur | Velvetleaf | Sicklepod | Black nightshade | Barnyardgrass | Green foxtail | Johnsongrass |
| (1) | 1.25 | 0 | 4 | 4 | 5 | 4 | 5 | 4 | 4 | 5 |
| | 0.32 | 0 | — | — | 4 | — | 5 | 4 | 4 | 5 |
| (2) | 5 | — | 5 | 4 | 5 | 4 | 5 | 4 | 5 | 5 |
| | 1.25 | 1 | 4 | 4 | — | — | 5 | 4 | 5 | 5 |
| (3) | 5 | — | 4 | 4 | 5 | 4 | 5 | 5 | 4 | 5 |
| | 1.25 | 0 | — | — | 4 | — | 5 | 4 | 4 | 5 |
| (4) | 1.25 | 1 | 4 | — | 5 | 4 | 5 | 5 | 5 | 5 |
| | 0.32 | 0 | 4 | — | 5 | 4 | 5 | 5 | 5 | 5 |

TABLE 11-continued

| Test compound | Dosage rate of active ingredient (g/a) | Phyto-toxicity Corn | Herbicidal activity | | | | | | | |
|---|---|---|---|---|---|---|---|---|---|---|
| | | | Tall morning-glory | Cockle-bur | Velvet-leaf | Sickle-pod | Black nightshade | Barnyard-grass | Green foxtail | Johnson-grass |
| (9) | 5 | 0 | 4 | — | 5 | 4 | 5 | 4 | 4 | 4 |
| | 1.25 | 0 | — | — | 5 | — | 5 | — | 4 | 4 |
| (10) | 1.25 | 1 | 4 | 4 | 5 | 4 | 5 | 4 | 4 | 4 |
| | 0.32 | 0 | 4 | — | 5 | 4 | 5 | 4 | 4 | 4 |
| (11) | 1.25 | 1 | 4 | — | 5 | 4 | 5 | 5 | 4 | 4 |
| | 0.32 | 1 | — | — | 4 | — | 5 | 5 | 4 | 4 |
| A | 5 | 1 | 1 | 0 | 0 | 1 | — | 2 | 0 | 2 |
| B | 5 | 0 | 0 | 0 | 0 | 0 | 0 | 0 | 0 | 0 |
| C | 5 | 0 | 1 | 0 | 3 | 2 | 3 | 2 | 1 | 2 |
| E | 5 | 4 | 0 | 0 | — | 1 | 3 | 4 | 2 | — |
| | 1.25 | 2 | 0 | 0 | 1 | 0 | 2 | 2 | 0 | 3 |
| M | 1.25 | 3 | 4 | — | 4 | 4 | 5 | 5 | 5 | 5 |
| | 0.32 | 1 | 3 | — | — | 2 | 2 | 3 | 2 | 3 |

TEST EXAMPLE 7

Soil treatment test in upland field soil

Vats of 33×23 cm² in area and 11 cm in depth were filled with upland field soil, and the seeds of beet, wheat, barley, pale smartweed, cleavers, chickweed, birdseye speedwell, field pansy, downy brome, wild oat, blackgrass and annual bluegrass were sowed in the respective vats and covered with soil in a thickness of 1 to 2 cm. The test compounds were formulated into emulsifiable concentrates according to Formulation example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in Table 12.

TEST EXAMPLE 8

Foliar treatment test in upland field soil

Vats of 33×23 cm² in area and 11 cm in depth were filled with upland field soil, and the seeds of wheat, pale smartweed, cleavers, chickweed, birdseye speedwell, field pansy, downy brome, wild oat, blackgrass and annual bluegrass were sowed in the respective vats and cultivated for 31 days. Thereafter, the test compounds were formulated into emulsifiable concentrates according to Formulation example 2, and the prescribed amount of each emulsifiable concentrate was diluted with water corresponding to 10 liters/are and uniformly applied from above onto the whole foliar portion of the test plants by means of an automatic sprayer. The condition of growth of the weeds and crop at that time varied with the kind of the test plants, but the test plants were in the 1- to 4-leaf stage and were 3 to 25 cm in height. Twenty-five days after application, the herbicidal activity and phytotoxicity were examined. The results are shown in Table 13. This test was carried out in a greenhouse through the whole test period.

TABLE 12

| Test compound | Dosage rate of active ingredient (g/a) | Phytotoxicity | | | Herbicidal activity | | | | | | | |
|---|---|---|---|---|---|---|---|---|---|---|---|---|
| | | Beet | Wheat | Barley | Pale smartweed | Cleavers | Chick-weed | Birdseye speedwell | Field pansy | Downy brome | Wild oat | Black-grass | Annual bluegrass |
| (1) | 2.5 | — | 1 | 0 | 4 | 5 | 5 | 5 | 4 | 5 | 4 | 5 | 4 |
| | 0.63 | — | 0 | 0 | 4 | 5 | — | 5 | 4 | 5 | 4 | 5 | 4 |
| (2) | 2.5 | — | — | — | 4 | 4 | 4 | 5 | 4 | 5 | 4 | 4 | 4 |
| | 0.63 | — | 0 | 1 | — | — | — | 5 | 4 | 5 | — | 4 | 4 |
| (3) | 2.5 | — | 1 | — | 4 | — | — | 4 | — | 5 | 4 | — | 4 |
| | 0.63 | — | 0 | — | — | — | — | 4 | — | 4 | — | — | 4 |
| (4) | 2.5 | 0 | 0 | 0 | — | — | 4 | — | — | 4 | — | — | — |
| (5) | 2.5 | 0 | 0 | 0 | 4 | — | — | 4 | 4 | 4 | — | — | 4 |
| (10) | 2.5 | — | — | — | 4 | 4 | 5 | 5 | 5 | 4 | 4 | 4 | 4 |
| | 0.63 | — | 1 | 1 | 4 | — | 4 | 5 | 4 | — | — | 4 | 4 |
| (11) | 2.5 | 1 | — | 0 | 4 | — | — | 4 | 4 | 4 | 4 | 4 | 4 |
| (14) | 2.5 | 1 | — | — | 4 | — | — | 5 | — | 5 | 4 | 5 | 4 |
| | 0.63 | 0 | 1 | 1 | — | — | — | 4 | — | 4 | 4 | 4 | 4 |
| A | 2.5 | 2 | 2 | 3 | 1 | 1 | 0 | 1 | 0 | — | 1 | 3 | 3 |
| B | 2.5 | 0 | 0 | 0 | 0 | 0 | 0 | 0 | 0 | 0 | 0 | 0 | 0 |
| C | 2.5 | 3 | 3 | 3 | 3 | 3 | 3 | 3 | 1 | — | 3 | 3 | 3 |
| D | 2.5 | 2 | 0 | 2 | 0 | 0 | 0 | 2 | 0 | — | 2 | 2 | 3 |
| E | 2.5 | 4 | 4 | 4 | — | 2 | 2 | — | — | — | 3 | 3 | — |
| | 0.63 | 4 | 2 | 4 | 3 | 2 | 1 | 3 | 3 | 3 | 3 | 3 | — |
| G | 2.5 | 0 | 0 | 0 | 1 | 0 | 0 | 3 | 2 | 0 | 0 | 0 | — |
| | 0.63 | 0 | 0 | 0 | 0 | 0 | 0 | 0 | 1 | 0 | 0 | 0 | 1 |
| L | 2.5 | 3 | 0 | 2 | 1 | 0 | 2 | — | 0 | 2 | 0 | 0 | 3 |
| | 0.63 | 0 | 0 | 0 | 0 | 0 | 0 | — | 0 | 0 | 0 | 0 | 0 |

TABLE 13

| Test compound | Dosage rate of active ingredient (g/a) | Phytotoxicity Wheat | Herbicidal activity | | | | | | | | |
|---|---|---|---|---|---|---|---|---|---|---|---|
| | | | Plae smartweed | Cleavers | Chickweed | Birdseye speedwell | Field pansy | Downy brome | Wild oat | Blackgrass | Annual bluegrass |
| (1) | 2.5 | — | 4 | 4 | 4 | 4 | 4 | 4 | 4 | 4 | 4 |
| | 0.63 | 0 | 4 | — | — | 4 | 4 | 4 | — | 4 | 4 |
| (2) | 2.5 | — | 4 | 4 | — | 5 | 5 | 5 | 5 | 4 | 4 |
| | 0.63 | 1 | 4 | — | — | 4 | 4 | 4 | — | 4 | 4 |
| (3) | 2.5 | — | 4 | 4 | — | 4 | 4 | — | — | — | 4 |
| (4) | 2.5 | — | 4 | 4 | 5 | 5 | 4 | 4 | 4 | 4 | 4 |
| | 0.63 | — | 4 | — | 5 | 4 | 4 | 4 | 4 | 4 | 4 |
| (10) | 2.5 | — | 4 | 5 | 4 | 4 | 5 | — | — | — | 4 |
| A | 2.5 | 2 | 2 | — | 0 | 3 | — | 3 | 3 | 2 | 2 |
| | 0.63 | 1 | 1 | 1 | 0 | 1 | 0 | 1 | 1 | 1 | 0 |
| B | 2.5 | 0 | 0 | 0 | 0 | 0 | 0 | 0 | 0 | 0 | 0 |
| C | 2.5 | 3 | 2 | 0 | 0 | 3 | — | — | 3 | — | 2 |
| | 0.63 | 2 | 0 | 0 | 0 | 0 | 0 | 3 | 2 | 3 | 1 |
| D | 2.5 | 0 | 0 | 0 | 0 | 0 | 0 | 0 | 0 | 0 | 0 |
| F | 2.5 | — | 2 | — | 2 | 3 | — | 3 | 3· | 2 | 2 |
| | 0.63 | 2 | 2 | — | 2 | 2 | 2 | 2 | — | 2 | 2 |

TEST EXAMPLE 9

Flooding treatment test in paddy field

Cylindrical plastic pots of 8 cm in diameter and 12 cm in depth were filled with paddy field soil, and the seeds of barnyardgrass and bulrush were sowed 1 to 2 cm deep under the soil surface. After creating the state of paddy field by flooding, the tuber of arrowhead was buried 1 to 2 cm deep under the soil surface and cultivated in a greenhouse. After 6 days (at the initial stage of generation of every weed), the test compounds were formulated into emulsifiable concentrates according to Formulation example 2, and the prescribed amount of each emulsifiable concentrate was diluted with 2,5 ml of water and applied onto the water surface. After application, the test plants were cultivated for 19 days in a greenhouse, and the herbicidal activity was examined The results are shown in Table 14.

TABLE 14

| Test compound | Dosage rate of active ingredient (g/a) | Herbicidal activity | | |
|---|---|---|---|---|
| | | Barnyardgrass | Bulrush | Arrowhead |
| (12) | 0.16 | 4 | 4 | 4 |
| | 0.04 | 4 | 4 | 4 |
| (13) | 0.16 | 5 | 4 | 4 |
| | 0.04 | 4 | 4 | 4 |
| H | 0.16 | 3 | 3 | 3 |
| | 0.04 | 0 | 0 | 2 |
| K | 0.16 | 0 | 0 | 2 |
| | 0.04 | 0 | 0 | 1 |

TEST EXAMPLE 10

Soil treatment test in upland field soil

Vats of 33×23 cm² in area and 11 cm in depth were filled with upland field soil, and the seeds of tall morningglory, velvetleaf, sicklepod, black nightshade, barnyardgrass, green foxtail and johnsongrass were sowed in the respective vats and covered with soil in a thickness of 1 to 2 cm. The test compounds were formulated into emulsifiable concentrates according to Formulation example 2, and the prescribed amount of each emulsifiable concentrate was diluted with water corresponding to 10 liters/are and uniformly applied onto the whole soil surface by means of an automatic sprayer. 18 After application, the test plants were cultivated for days in a greenhouse, and the herbicidal activity was examined. The results are shown in Table 15.

TABLE 15

| Test compound | Dosage rate of active ingredient (g/a) | Herbicidal activity | | | | | | |
|---|---|---|---|---|---|---|---|---|
| | | Tall morningglory | Black nightshade | Velvetleaf | Sicklepod | Barnyardgrass | Green foxtail | Johnsongrass |
| (12) | 0.63 | 4 | 5 | 4 | 4 | 5 | 5 | 5 |
| | 0.16 | 4 | 5 | 4 | 4 | 4 | 5 | 4 |
| (13) | 0.63 | — | 5 | 4 | — | 4 | 5 | 5 |
| | 0.16 | — | 4 | 4 | — | 4 | 4 | 4 |
| E | 0.63 | 0 | — | 2 | 0 | 3 | — | — |
| | 0.16 | 0 | 3 | 1 | 0 | 1 | 2 | 2 |
| F | 0.63 | 1 | — | 2 | 2 | 3 | 3 | 3 |
| | 0.16 | 0 | 2 | 1 | 0 | 1 | 1 | 1 |
| G | 0.63 | 0 | 1 | 0 | 1 | 1 | 1 | 2 |
| | 0.16 | 0 | 0 | 0 | 0 | 0 | 0 | 0 |
| K | 0.63 | 0 | 2 | 3 | 0 | 2 | 3 | 3 |
| | 0.16 | 0 | 0 | 1 | 0 | 0 | 0 | 1 |

TEST EXAMPLE 11

Foliar treatment test in upland field soil

Vats of 33≦23 cm² in area and 11 cm in depth were filled with upland field soil, and the seeds of tall morningglory, velvetleaf, black nightshade, barnyardgrass, green foxtail and johnsongrass were sowed in the respective vats and cultivated for 16 days. Thereafter, the test compounds were formulated into emulsifiable concentrates according to Formulation example 2, and the prescribed amount of each emulsifiable concentrate was diluted with water corresponding to 10 liters/are and uniformly applied from above onto the whole foliar portion of the test plants by means of an automatic sprayer. The condition of growth of the weeds and crop at that time varied with the kind of the test plants, but the test plants were in the 0.5- to 4-leaf stage and were 4 to 27 cm in height. Eighteen days after application, the herbicidal activity was examined. The results are shown in Table 16. This test was carried out in a greenhouse through the whole test period.

TABLE 16

| Test compound | Dosage rate of active ingredient (g/a) | Herbicidal activity | | | | | |
|---|---|---|---|---|---|---|---|
| | | Tall morning-glory | Velvet-leaf | Black night-shade | Barnyard-grass | Green foxtail | Johnson-grass |
| (12) | 0.32 | 5 | 5 | 5 | 4 | 5 | 5 |
| | 0.08 | 4 | 5 | 5 | 4 | 4 | 4 |
| (13) | 0.32 | 4 | 5 | 5 | 4 | 4 | 5 |
| | 0.08 | — | 5 | 4 | 4 | — | 4 |
| G | 0.32 | 3 | — | — | 3 | 1 | 3 |
| | 0.08 | 1 | 2 | 2 | 1 | 0 | 1 |
| K | 0.32 | 3 | — | — | — | 1 | — |
| | 0.08 | 1 | 3 | 2 | 1 | 0 | 2 |
| L | 0.32 | 3 | — | 2 | 2 | — | 3 |
| | 0.08 | 1 | 2 | 0 | 0 | 1 | 0 |

TEST EXAMPLE 12

Soil treatment test in upland field soil

Vats of $33 \times 23$ cm² in area and 11 cm in depth were filled with upland field soil, and the seeds of pale smartweed, chickweed, birdseye speedwell, field pansy, wild oat, blackgrass and annual bluegrass were sowed in the respective vats and covered with soil in a thickness of 1 to 2 cm. The test compounds were formulated into emulsifiable concentrates according to Formulation example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity was examined. The results are shown in Table 17.

TABLE 17

| Test compound | Dosage rate of active ingredient (g/a) | Herbicidal activity | | | | | | |
|---|---|---|---|---|---|---|---|---|
| | | Pale smartweed | Chick-weed | Birdseye speedwell | Field pansy | Wild oat | Black-grass | Annual bluegrass |
| (12) | 0.16 | 4 | 4 | 5 | 4 | 4 | 4 | 4 |
| | 0.04 | 4 | 4 | 4 | 4 | — | — | — |
| (13) | 0.16 | 4 | 5 | 4 | 5 | 4 | 4 | 4 |
| | 0.04 | 4 | — | 4 | 4 | 4 | — | 4 |
| F | 0.16 | 1 | 0 | 3 | 1 | 1 | 2 | — |
| | 0.04 | 0 | 0 | 0 | 0 | — | — | 2 |
| K | 0.16 | 2 | 1 | — | — | 2 | 1 | 0 |
| | 0.04 | 0 | 0 | — | 2 | — | — | 0 |

TEST EXAMPLE 13

Foliar treatment test in upland field soil

Vats of $33 \times 23$ cm² in area and 11 cm in depth were filled with upland field soil, and the seeds of pale smartweed, cleavers, chickweed and field pansy were sowed in the respective vats and cultivated for 31 days. Thereafter, the test compounds were formulated into emulsifiable concentrates according to Formulation example 2, and the prescribed amount of each emulsifiable concentrate was diluted with water corresponding to 10 liters/are and uniformly applied from above onto the whole foliar portion of the test plants by means of an automatic sprayer. The condition of growth of the weeds and crop at that time varied with the kind of the test plants, but the test plants were in the 1- to 4-leaf stage and were 4 to 22 cm in height. Twenty-five days after application, the herbicidal activity was examined. The results are shown in Table 18. This test was carried out in a greenhouse through the whole test period.

TABLE 18

| Test compound | Dosage rate of active ingredient (g/a) | Herbicidal activity | | | |
|---|---|---|---|---|---|
| | | Pale smartweed | Cleavers | Chick-weed | Field pansy |
| (12) | 0.32 | 5 | 5 | 5 | 5 |
| | 0.08 | 4 | 5 | 4 | 4 |
| (13) | 0.32 | 5 | 5 | 5 | 5 |
| | 0.08 | 4 | — | 4 | 4 |
| G | 0.32 | 2 | 2 | 1 | 2 |
| | 0.08 | 1 | 1 | 0 | 1 |

What is claimed is:

1. A pyrimidine derivative represented by the formula,

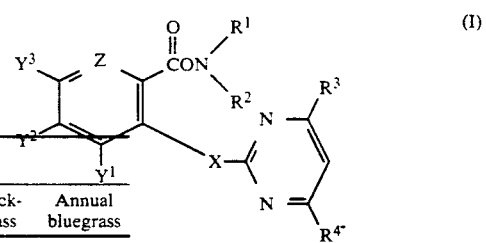

wherein each of $R^1$ and $R^2m$ which may be the same or different, represents a hydrogen atom, a $C_1$–$C_6$ alkyl group, a $C_3$–$C_6$ alkenyl group, a $C_3$–$C_6$ alkynyl group, a halo $C_1$–$C_6$ alkyl group, a $C_1$–$C_6$ alkoxy $C_1$–$C_6$ alkyl group, a $C_3$–$C_6$ alkenyloxy $C_1$–$C_6$ alkyl group, a $C_3$–$C_6$ alkynyloxy $C_1$–$C_6$ alkyl group, a $C_1$–$C_6$ alkoxycarbonyl $C_1$–$C_6$ alkyl group, a $C_3$–$C_6$ alkenyloxycarbonyl $C_1$–$C_6$ alkyl group, a $C_3$–$C_6$ alkynyloxycarbonyl $C_1$–$C_6$ alkyl group, a cyano $C_1$–$C_6$ alkyl group, a group represented by the formula,

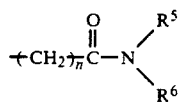

(in which each of $R^5$ and $R^6$, which may be the same or different, represents a hydrogen atom, a $C_1$–$C_6$ alkyl group, a $C_3$–$C_6$ alkenyl group or a $C_3$–$C_6$ alkynyl group, and n represents an integer of 1, 2, 3, or 4), a group represented by the formula

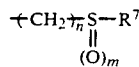

(in which n is as defined above, $R^7$ represents a $C_1$–$C_6$ alkyl group, a $C_3$–$C_6$ alkenyl group or a $C_3$–$C_6$ alkynyl group, and m represents an integer of 0, 1 or 2), a cyclo $C_3$–$C_8$ alkyl group, or an optionally substituted phenyl group, an optionally substituted benzyl group, or $R^1$ and $R^2$, bonded together at their ends, form an optionally substituted $C_4$–$C_7$ alkylene group or an optionally substituted $C_3$–$C_6$ alkyene group containing hetero atom; the hetero atom in $R^1$ and $R^2$ means a nitrogen atom, an oxygen atom or a sulfur atom; each of $R^3$ and $R^4$, which may be the same or different, represents a $C_1$–$C_6$ alkyl group, a $C_1$–$C_6$ alkoxy group, a halo $C_1$–$C_6$ alkoxy group or a halogen atom; X represents an oxygen atom or a sulfur atom; Z represents N or $CY^4$; each of $Y^1$, $Y^2$, $Y^3$, which may be the same or different, represents a hydrogen atom, a halogen atom, a $C_1$–$C_6$ alkyl group, or a $C_1$–$C_6$ alkoxy group; and $Y^4$ represents a hydrogen atom, a hydroxyl group, a mercapto group, a nitro group, a halogen atom, a $C_1$–$C_6$ alkyl group, a $C_2$–$C_6$ alkenyl group, a $C_2$–$C_6$ alkynyl group, a $C_1$–$C_6$ alkoxy group, a $C_3$–$C_4$ alkenyloxy group, a $C_3$–$C_6$ alkynyloxy group, a halo $C_1$–$C_6$ alkyl group, a halo $C_2$–$C_6$ alkenyl group, a halo $C_2$–$C_6$ alkynyl group, a halo $C_1$–$C_6$ alkoxy group, a halo $C_3$–$C_6$ alkenyloxy group, a halo $C_3$–$C_6$ alkynyloxy group, a $C_1$–$C_6$ alkoxy $C_1$–$C_6$ alkyl group, a $C_3$–$C_6$ alkenyloxy $C_1$–$C_6$ alkyl group, a $C_3$–$C_6$ alknyloxy $C_1$–$C_6$ alkyl group, a cyano group, a formyl group, a carboxyl group, a $C_1$–$C_6$ alkoxycarbonyl group, a $C_3$–$C_6$ alkenyloxycarbonyl group, a $C_3$–$C_6$ alkynyloxycarbonyl group; an optionally a substituted phenyl group, an optionally substituted phenoxy group, an optionally substituted phenylthio group, an optionally substituted benzyloxy group, an optionally substituted benzylthio group, a group represented by the formula,

(in which $R^5$ and $R^6$ are as defined above), a group represented by the formula,

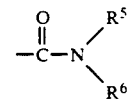

(in which $R^5$ and $R^6$ are as defined above),

(in which $R^7$ and m are as defined above), a group represented by the formula

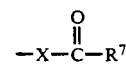

(in which $R^7$ and X are as defined above), or a group represented by the formula,

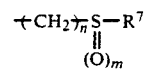

(in which $R^7$, m and n are as defined above), each optionally substituted group in the above being substituted with a $C_1$–$C_6$ alkyl group, a $C_1$–$C_6$ alkoxy group, a halo $C_1$–$C_6$ alkyl group, a $C_1$–$C_6$ alkoxycarbonyl group or a halogen atom.

2. A pyrimidine derivative according to claim 1, wherein each of $R^3$ and $R^4$, which may be the same or different, is a $C_1$–$C_6$ alkoxy group.

3. A pyrimidine derivative according to claim 2, wherein both $R^3$ and $R^4$ are a methoxy group.

4. A pyrimidine derivative according to claim 1, wherein X is an oxygen atom.

5. A pyrimidine derivative according to claim 1, wherein Z is N or $CY^5$ represents a hydrogen atom, a halo $C_1$–$C_6$ alkyl group or a halogen atom).

6. A pyrimidine derivative according to claim 5, wherein Z is $CY^5$ (in which $Y^5$ is a halo $C_1$–$C_6$ alkyl group or a halogen atom).

7. A pyrimidine derivative according to claim 6, wherein $Y^5$ is a halogen atom.

8. A pyrimidine derivative according to claim 1, wherein $Y^1$, $Y^2$ and $Y^3$ are a hydrogen atom or a fluorine atom.

9. A pyrimidine derivative according to claim 5, wherein each of $R^3$ and $R^4$ are a methoxy group, X is an oxygen atom.

10. A pyrimidine derivative according to claim 6, wherein each of $R^3$ and $R^4$ are a methoxy group, X is an oxygen atom.

11. A pyrimidine derivative according to claim 7, wherein each of $R^3$ and $R^4$ are a methoxy group, X is an oxygen atom.

12. A pyrimidine derivative according to claim 8, wherein each of $R^3$ and $R^4$ are a methoxy group, X is an oxygen atom.

13. A pyrimidine derivative according to claim 5, wherein each of $R^3$ and $R^4$ are a methoxy group, X is a oxygen atom, and each of $Y^1$, $Y^2$ and $Y^3$ are a hydrogen atom or a fluorine atom.

14. A pyrimidine derivative according to claim 1 selected from the following compound group:

4,6-dimethoxy-2-{2-(N,N-dimethylaminooxycarbonyl)phenoxy}pyrimidine, 4,6-dimethoxy-2-{3-chloro-2-(N,N-dimethylaminooxycarbonyl)phenoxy}pyrimidine, 4,6-dimethoxy-2-{3-fluoro-2-(N,N-dimethylaminooxycarbonyl)phenoxy}pyrimidine, 3-(4,6-dimethoxypyrimidin-2-yl)oxy-2-(N,N-dimethylaminooxycarbonyl)pyridine, 4,6-dimethoxy-2-(3-trifluoromethyl-2-(N,N-dimethylaminooxycarbonyl)phenoxy)pyrimidine, 4,6-dimethoxy-2-{3-chloro-2-(1-piperidyloxycarbonyl)phenoxy}pyrimidine and 4,6-dimethoxy-2-{3-chloro-2-(N-tert-butylaminooxycarbonyl)phenoxy}pyrimidine.

15. A herbicidal composition which comprises as an active ingredient a herbicidally effective amount of the compound (I) according to claim 1 and an inert carrier or a diluent.

16. A method for controlling undesired weeds, which comprises applying a herbicidally effective amount of the compound (I) according to claim 1 and an inert carrier or a diluent to the area where undesired weeds grow or will grow.

* * * * *